United States Patent
Festersen et al.

(10) Patent No.: US 9,279,165 B2
(45) Date of Patent: Mar. 8, 2016

(54) MASHING PROCESS

(71) Applicant: Novozymes A/S, Bagsvaerd (DK)

(72) Inventors: Rikke Monica Festersen, Slangerup (DK); Anders Viksoe Nielsen, Slangerup (DK); Christel Thea Joergensen, Lyngby (DK); Lars Lehmann Hylling Christensen, Alleroed (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/191,868

(22) Filed: Feb. 27, 2014

(65) Prior Publication Data

US 2014/0170712 A1   Jun. 19, 2014

Related U.S. Application Data

(63) Continuation of application No. 12/493,587, filed on Jun. 29, 2009, now Pat. No. 8,679,791, which is a continuation of application No. 10/583,676, filed as application No. PCT/DK2004/000880 on Dec. 17, 2004, now abandoned.

(60) Provisional application No. 60/531,337, filed on Dec. 19, 2003.

(30) Foreign Application Priority Data

Dec. 19, 2003   (DK) .................. 2003 01895

(51) Int. Cl.

| | | |
|---|---|---|
| *C12C 1/00* | (2006.01) | |
| *C12N 9/42* | (2006.01) | |
| *C12N 9/24* | (2006.01) | |
| *C12C 3/08* | (2006.01) | |
| *C12H 1/14* | (2006.01) | |
| *A23L 1/28* | (2006.01) | |
| *C07H 21/04* | (2006.01) | |
| *C07K 1/00* | (2006.01) | |
| *C21C 7/04* | (2006.01) | |
| *A23K 1/16* | (2006.01) | |
| *A23K 1/165* | (2006.01) | |
| *A23L 1/09* | (2006.01) | |
| *C12C 5/00* | (2006.01) | |
| *C12C 7/16* | (2006.01) | |

(52) U.S. Cl.
CPC ............. *C21C 7/04* (2013.01); *A23K 1/1643* (2013.01); *A23K 1/1653* (2013.01); *A23L 1/095* (2013.01); *C12C 5/004* (2013.01); *C12C 7/16* (2013.01); *C12N 9/248* (2013.01); *C12N 9/2437* (2013.01); *C12Y 302/01004* (2013.01); *C12Y 302/01008* (2013.01)

(58) Field of Classification Search
CPC .... A23K 1/1643; A23K 1/1653; A23L 1/095; C12C 5/004; C12C 7/16; C12C 7/04; C12N 9/248; C12N 9/2437; C12Y 302/01004; C12Y 302/01008

USPC .......... 435/93, 209, 200; 426/13, 16, 592, 64; 536/23.2; 530/350
See application file for complete search history.

(56) References Cited

U.S. PATENT DOCUMENTS

| | | | |
|---|---|---|---|
| 4,110,163 | A | 8/1978 | Hjortshoj et al. |
| 4,238,345 | A | 12/1980 | Guilbert |
| 4,746,517 | A | 5/1988 | Ducroo |
| 5,693,518 | A | 12/1997 | Kofod |
| 5,874,274 | A | 2/1999 | Jakobsen et al. |
| 6,080,567 | A | 6/2000 | Kofod et al. |
| 6,197,564 | B1 | 3/2001 | Kofod |
| 6,562,340 | B1 | 5/2003 | Bedford et al. |
| 6,623,949 | B1 | 9/2003 | Gualfetti et al. |
| 2002/0164399 | A1 | 11/2002 | Souppe et al. |
| 2003/0053999 | A1 | 3/2003 | Jonniaux et al. |
| 2005/0054071 | A1 | 3/2005 | Udagawa |
| 2007/0148741 | A1 | 6/2007 | Festersen |

FOREIGN PATENT DOCUMENTS

| | | |
|---|---|---|
| EP | 0910620 | 8/2002 |
| EP | 2258829 | 8/2010 |
| FR | 2786784 | 6/2000 |
| GB | 2021142 | 11/1979 |
| SU | 614130 | 7/1978 |
| WO | 9516782 A1 | 6/1995 |
| WO | 9523514 A1 | 9/1995 |
| WO | 97/18286 A1 | 5/1997 |
| WO | 97/27291 A1 | 7/1997 |
| WO | 97/27292 A1 | 7/1997 |
| WO | 97/42302 A1 | 11/1997 |
| WO | 98/05788 A1 | 2/1998 |
| WO | 99/31255 A2 | 6/1999 |
| WO | 0212462 | 2/2002 |
| WO | 02/074895 A2 | 9/2002 |

(Continued)

OTHER PUBLICATIONS

Hong et al., Cloning of a gene encoding a thermo-stable endo-b-1-4-glucanase from Thermoascus aurantiacus and its expression in yeast. Biotechnol. Lett., 2003, vol. 25: 657-661.*
Van Petegem et al., Atomic resolution structure of the major endoglucanase from Thermoascus aurantiacus. Biochem. Biophys. Res. Commun., 2002, vol. 296: 161-166.*
Broun et al., Science, vol. 282, pp. 1315-1317 (1998).
Chica et al., Curr. Opi. Biotechnol, vol. 16, pp. 378-384 (2005).
Devos et al., Proteins Structure and Genetics, vol. 41, pp. 98-107 (2000).

(Continued)

*Primary Examiner* — Ganapathirama Raghu
(74) *Attorney, Agent, or Firm* — Kristin McNamara

(57) ABSTRACT

The present invention relates to a mashing and filtration step in a brewing process and to a composition useful in the mashing and filtration step of a brewing process.

15 Claims, No Drawings

(56) References Cited

FOREIGN PATENT DOCUMENTS

| WO | 03/062409 A2 | 7/2003 |
| WO | 2005059084 A1 | 6/2005 |

OTHER PUBLICATIONS

Henrissat & Davies, Current Opinion in Structural Biology, vol. 7, pp. 637-644 (1997).

Schulein et al., Journal of Bacteriology, vol. 57, pp. 71-81 (1997).
Seffernick et al., J. Bacteriol, vol. 183, No. 8, pp. 2405-2410 (2001).
Sen et al., Appl. Biochem, Biotechnol, vol. 143, pp. 212-223 (2007).
Whisstock et al., Q. Rev Biophysics, vol. 36, No. 3, pp. 307-340 (2003).
Wishart et al., J. Biol. Chem. vol. 270, No. 45, pp. 26782-26785 (1995).
Witkowski et al., Biochemistry, vol. 38, pp. 11643-11650 (1999).

\* cited by examiner

MASHING PROCESS

CROSS-REFERENCE TO RELATED APPLICATIONS

This application is a continuation of U.S. application Ser. No. 12/493,587 filed on Jun. 29, 2009 (now U.S. Pat. No. 8,679,791), which is a continuation of U.S. application Ser. No. 10/583,676 filed on Jun. 19, 2006 (abandoned), which is a 35 U.S.C. 371 national application of PCT/DK2004/000880 filed Dec. 17, 2004, which claims priority or the benefit under 35 U.S.C. 119 of Danish application no. PA 2003 01895 filed Dec. 19, 2003 and U.S. provisional application No. 60/531,337 filed Dec. 19, 2003, the contents of which are fully incorporated herein by reference.

FIELD OF THE INVENTION

The present invention relates, inter alia, to a mashing and filtration step in a process for the production of an alcoholic beverage, such as beer or whiskey, and to a composition useful in the mashing and filtration step in such a process.

BACKGROUND OF THE INVENTION

The use of enzymes in brewing is common. Application of enzymes to the mashing step to improve mash filterability and increase extract yield is described in WO 97/42302. However, there is a need for improvement of the mashing and filtration step and for improved enzymatic compositions for use in the mashing and filtration step.

SUMMARY OF THE INVENTION

The invention provides a process for production of a mash having enhanced filterability and/or improved extract yield after filtration, which comprises; preparing a mash in the presence of enzyme activities and filtering the mash to obtain a wort, wherein the enzyme activities comprise; a xylanase of glucoside hydrolase family 10 present in an amount of at least 15% w/w of the total xylanase and endoglucanase enzyme protein.

In a further aspect the invention provides a process of reducing the viscosity of an aqueous solution comprising a starch hydrolysate, said process comprising: testing at least one xylanolytic enzyme for its hydrolytic activity towards insoluble wheat arabinoxylan, selecting a xylanolytic enzyme which cleaves next to branched residues thereby leaving terminal substituted xylose oligosaccharides, and adding the selected xylanolytic enzyme to the aqueous solution comprising a starch hydrolysate.

In an even further aspect the invention provides a process of reducing the viscosity of an aqueous solution comprising a starch hydrolysate, said process comprising: testing at least one endoglucanolytic enzyme for its hydrolytic activity towards barley beta-glucan, selecting a endoglucanolytic enzyme which under the conditions: 10 microgram/ml purified enzyme and 5 mg/ml barley beta-glucan in 50 mM sodium acetate, 0.01% Triton X-100, at pH 5.5 and 50° C., within 1 hour degrades more than 70% of the barley beta-glucan to DP 6 or DP<6, and adding the selected endoglucanolytic enzyme to the aqueous solution comprising a starch hydrolysate.

In yet a further aspect the invention provides a composition comprising; a GH10 xylanase present in an amount of at least 15% w/w of the total enzyme protein; and/or, a GH12, GH7 and/or GH5 endoglucanase present in an amount of at least 40% w/w of the total enzyme protein.

Other aspects include the use of the composition of the proceeding aspect in a process of comprising reduction of the viscosity of an aqueous solution comprising a starch hydrolysate, including such processes wherein the aqueous solution comprising a starch hydrolysate is a mash for beer making, or wherein the aqueous solution comprising a starch hydrolysate is intended for use in a feed composition.

DETAILED DESCRIPTION OF THE INVENTION

Definitions

Throughout this disclosure, various terms that are generally understood by those of ordinary skill in the arts are used. Several terms are used with specific meaning, however, and are meant as defined by the following.

As used herein the term "grist" is understood as the starch or sugar containing material that's the basis for beer production, e.g. the barley malt and the adjunct.

The term "malt" is understood as any malted cereal grain, in particular barley. The term "adjunct" is understood as the part of the grist which is not barley malt.

The adjunct may be any carbohydrate rich material.

The term "mash" is understood as a aqueous starch slurry, e.g. comprising crushed barley malt, crushed barley, and/or other adjunct or a combination hereof, steeped in water to make wort.

The term "wort" is understood as the unfermented liquor run-off following extracting the grist during mashing.

The term "spent grains" is understood as the drained solids remaining when the grist has been extracted and the wort separated from the mash.

The term "beer" is here understood as fermented wort, e.g. an alcoholic beverage brewed from barley malt, optionally adjunct and hops.

The term "extract recovery" in the wort is defined as the sum of soluble substances extracted from the grist (malt and adjuncts) expressed in percentage based on dry matter.

The term "a thermostable enzyme" is understood as an enzyme that under the temperature regime and the incubation period applied in the processes of the present invention in the amounts added is capable of sufficient degradation of the substrate in question.

The term "Type A xylanase" is understood as a xylanase that cleaves arabinoxylan polymers close to branched residues leaving terminal substituted xylose oligosaccharides. Type A xylanases may be identified using the method described in the Methods section of the present disclosure The term "homology" when used about polypeptide or DNA sequences and referred to in this disclosure is understood as the degree of homology between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453. The following settings for polypeptide sequence comparison are used: GAP creation penalty of 3.0 and GAP extension penalty of 0.1.

The term "DP" is the degree of polymerisation, herein used for average number of glucose units in polymers in a polysaccharide hydrolysate.

The numbering of Glycoside Hydrolase Families (GH) and Carbohydrate Binding Modules (CBM) applied in this disclosure follows the concept of Coutinho, P. M. & Henrissat, B. (1999) CAZy—Carbohydrate-Active Enzymes server at URL: afmb.cnrs-mrs.fr/~cazy/CAZY/ index.html or alternatively Coutinho, P. M. & Henrissat, B. 1999; The modular structure of cellulases and other carbohydrate-active enzymes: an integrated database approach. In "*Genetics, Biochemistry and Ecology of Cellulose Degradation*"., K. Ohmiya, K. Hayashi, K. Sakka, Y. Kobayashi, S. Karita and T. Kimura eds., Uni Publisher Co., Tokyo, pp. 15-23, and in Bourne, Y. & Henrissat, B. 2001; Glycoside hydrolases and glycosyltransferases: families and functional modules, Current Opinion in Structural Biology 11:593-600. This classification system groups glucoside hydrolases based on similarities in primary structure. The members of a family furthermore show the same catalytic mechanism and have similarities in the overall three-dimensional structure, although a family may contain members with substantial variation in substrate specificity.

The naming of *Humicola insolens* endoglucanases follows the system of Karlsson, J. 2000. Fungal Cellulases, Study of hydrolytic properties of endoglucanases from *Trichoderma reesei* and *Humicola insolens*. Lund University.

Brewing processes are well-known in the art, and generally involve the steps of malting, mashing, and fermentation. In the traditional brewing process the malting serves the purpose of converting insoluble starch to soluble starch, reducing complex proteins, generating colour and flavour compounds, generating nutrients for yeast development, and the development of enzymes. The three main steps of the malting process are steeping, germination, and kilning.

Steeping includes mixing the barley kernels with water to raise the moisture level and activate the metabolic processes of the dormant kernel. In the next step, the wet barley is germinated by maintaining it at a suitable temperature and humidity level until adequate modification, i.e. such as degradation of starch and activation of enzymes, has been achieved. The final step is to dry the green malt in the kiln. The temperature regime in the kiln determines the colour of the barley malt and the amount of enzymes which survive for use in the mashing process. Low temperature kilning is more appropriate for malts when it is essential to preserve enzymatic activity. Malts kilned at high temperatures have very little or no enzyme activity but are very high in colouring such as caramelized sugars as well as in flavouring compounds.

Mashing is the process of converting starch from the milled barley malt and solid adjuncts into fermentable and unfermentable sugars to produce wort of the desired composition. Traditional mashing involves mixing milled barley malt and adjuncts with water at a set temperature and volume to continue the biochemical changes initiated during the malting process. The mashing process is conducted over a period of time at various temperatures in order to activate the endogenous malt enzymes responsible for the degradation of proteins and carbohydrates. By far the most important change brought about in mashing is the conversion of starch molecules into fermentable sugars. The principal enzymes responsible for starch conversion in a traditional mashing process are alpha- and beta-amylases. Alpha-amylase very rapidly reduces insoluble and soluble starch by splitting starch molecules into many shorter chains that can be attacked by beta-amylase. The disaccharide produced is maltose.

Traditionally lager beer has often been brewed using a method referred to as "step-infusion". This mashing procedure involves a series of rests at various temperatures, each favouring one of the necessary endogenous enzyme activities. To day the double-mash infusion system is the most widely used system for industrial production of beer, especially lager type beer. This system prepares two separate mashes. It utilizes a cereal cooker for boiling adjuncts and a mash tun for well-modified, highly enzymatically active malts.

When brewing from grists low in enzymes such as high adjunct grists, mashing may be performed in the presence of added enzyme compositions comprising the enzymes necessary for the hydrolysis of the grist starch. These enzymes may comprise alpha-amylases, pullulanases, beta-amylases and glucoamylases.

After mashing, it is necessary to separate the liquid extract (the wort) from the solids (spent grains i.e. the insoluble grain and husk material forming part of grist). Wort separation is important because the solids contain large amounts of non-starch polysaccharides, protein, poorly modified starch, fatty material, silicates, and polyphenols (tannins). Important non-starch polysaccharides present in cereal grains are beta-glucan and arabinoxylan. The endosperm cell wall of barley comprises 75% beta-glucan, 20% arabinoxylan, and 5% remaining protein with small amount of cellulose, glucomannan and phenolic acids. Long chains of barley arabinoxylans, and to a lesser degree beta-glucan, which have not been modified due to enzymatic hydrolysis may cause formation of gels when solubilised in water, these gels will strongly increase wort viscosity and reduce filterability. Likewise is it very important for the quality of the wort that the beta-glucan has been reduced to smaller oligomers, as unmodified beta-glucans later on will give rise to haze stability problems in the final beer. Therefore, enzymatic compositions comprising endoglucanases and xylanases, such as Ultraflo® or Viscozyme®, are often used in the mashing step to improve wort separation. The objectives of wort separation, inter alia, include the following:

to obtain good extract recovery,
to obtain good filterability, and
to produce clear wort.

Extraction recovery and filterability are important for the economy in the brewing process, while the wort clarity is a must in order to produce a beer which does not develop haze. Extraction recovery, filterability and wort clarity is greatly affected by the standard of the grist, e.g. the barley malt and the types of adjunct, as well as the applied mashing procedure.

Following the separation of the wort from the spent grains the wort may be fermented with brewers yeast to produce a beer.

Further information on conventional brewing processes may be found in "Technology Brewing and Malting" by Wolfgang Kunze of the Research and Teaching Institute of Brewing, Berlin (VLB), 2nd revised Edition 1999, ISBN 3-921690-39-0.

Embodiments of the Invention

The invention provides a process for production of a mash having enhanced filterability and/or improved extract yield after filtration, which comprises; preparing a mash in the presence of enzyme activities and filtering the mash to obtain a wort, wherein the enzyme activities comprise; a xylanase of GH family 10 present in an amount of at least 15%, 20%, preferably 25%, such as at least 30%, or at least 40%, at least 50% or at least 60% such as at least 70%, at least 80%, at least 90%, or even 100% w/w of the total xylanase and endoglucanase enzyme protein.

In a preferred embodiment the xylanase is a type A xylanase, and in a particular embodiment the xylanase is a type A xylanase having a $I_{1,3 terminal}/I_{1,3 internal}$ ratio of at least 0.25, such as at least 0.30, al least 0.40, at least 0.50, or even at least 0.60.

Preferably the xylanase has a CBM, preferably a CBM of family 1.

In another preferred embodiment the xylanase is a xylanase which in the xylanase binding assay described herein has a barley soluble/insoluble fibre binding ratio of at least 0.50, preferably at least 0.60, more preferably at least 0.70, such as 0.80, 0.90, 1.00, 1.10 or even at least 1.20.

In another preferred embodiment the xylanase is derived from a filamentous fungi such as from a strain of an *Aspergillus* sp., preferably from *Aspergillus aculeatus* (SEQ ID NO:8 or SEQ ID NO:9), from a strain of a *Myceliophotora* sp., preferably from a *Myceliophotora thermophilia* (SEQ ID NO:13), from a strain of a *Humicola* sp., preferably from *Humicola insolens* (SEQ ID NO:12). In yet another preferred embodiment the xylanase is derived from a strain of a *Trichoderma* sp., preferably from *T. reesei* such as the xylanase shown in SEQ ID NO:17 In a more preferred embodiment the xylanase the xylanase is derived from a has at least 50%, such as at least 60%, 70%, 80% or even 90% homology to any of the aforementioned sequences.

In another preferred embodiment the xylanase is derived from a bacterium such as from a strain of a *Bacillus*, preferably from *Bacillus halodurans*.

In another preferred embodiment the endoglucanase is an endoglucanase derived from *Humicola* sp., such as the endoglucanase from *Humicola insolens* (SEQ ID NO:3), or the endoglucanase from *H. insolens* (SEQ ID NO:4), from *Thermoascus* sp., such as the endoglucanase derived from *Thermoascus aurantiacus* (SEQ ID NO: 7), or from *Aspergillus* sp., such as the endoglucanase derived from *Aspergillus aculeatus* (SEQ ID NO:16).

In a preferred embodiment the xylanase has at least 50%, such as at least 60%, 70%, 80% or even 90% homology to any of the aforementioned sequences.

In another preferred embodiment at least one additional enzyme is present, which enzyme is arabinofuranosidase.

The invention also provides a process of reducing the viscosity of an aqueous solution comprising a starch hydrolysate, said process comprising: testing at least one xylanolytic enzyme for its hydrolytic activity towards insoluble wheat arabinoxylan, selecting a xylanolytic enzyme which cleaves next to branched residues thereby leaving terminal substituted xylose oligosaccharides, and adding the selected xylanolytic enzyme to the aqueous solution comprising a starch hydrolysate.

The invention further provides a process of reducing the viscosity of an aqueous solution comprising a starch hydrolysate, said process comprising: testing at least one endoglucanolytic enzyme for its hydrolytic activity towards barley beta-glucan, selecting a endoglucanolytic enzyme which under the conditions: 10 microgram/ml purified enzyme and 5 mg/ml barley beta-glucan in 50 mM sodium acetate, 0.01% Triton X-100, at pH 5.5 and 50° C., within 1 hour degrades more than 70% of the barley beta-glucan to DP 6 or DP<6, and adding the selected endoglucanolytic enzyme to the aqueous solution comprising a starch hydrolysate.

In preferred embodiments of the two processes the aqueous solution comprising a starch hydrolysate is a mash for beer making.

The invention also provides a composition comprising; a GH10 xylanase present in an amount of at least 15% w/w of the total enzyme protein; and/or, a GH12, GH7 and/or GH5 endoglucanase present in an amount of at least 40% w/w of the total enzyme protein.

In a preferred embodiment the xylanase of the composition is a type A xylanase, and preferably a type A xylanase having a $I_{1,3terminal}/I_{1,3internal}$ ratio of at least 0.25, such as at least 0.30, al least 0.40, at least 0.50, or even at least 0.60.

In a preferred embodiment the xylanase of the composition is derived from a filamentous fungi such as from a strain of an *Aspergillus* sp., preferably from *Aspergillus aculeatus* (SEQ ID NO:8 or SEQ ID NO:9), from a strain of a *Myceliophotora* sp., preferably from a *Myceliophotora thermophilia* (SEQ ID NO:13), from a strain of a *Humicola* sp., preferably from *Humicola insolens* (SEQ ID NO:12). In a preferred embodiment the xylanase of the composition has at least 50%, such as at least 60%, 70%, 80% or even 90% homology to any of the aforementioned sequences.

In a preferred embodiment the xylanase of the composition is derived from a bacterium such as from a strain of a *Bacillus*, preferably from *Bacillus halodurans*.

In a preferred embodiment the endoglucanase of the composition is an endoglucanase derived from *Humicola* sp., such as the endoglucanase from *Humicola insolens* (SEQ ID NO:3), the endoglucanase from *H. insolens* (SEQ ID NO:4) or from *Thermoascus* sp., such as the endoglucanase derived from *Thermoascus aurantiacus* (SEQ ID NO: 7), or from *Aspergillus* sp., such as the endoglucanase derived from *Aspergillus aculeatus* (SEQ ID NO:16), or from *Trichoderma* sp. preferably from *T. reesei* and/or *T. viride*, such as the family 5 endoglucanase shown in SEQ ID NO:18, the family 7, beta-glucanase shown in SEQ ID NO:19 or the fam 12, beta-glucanase shown in SEQ ID NO:20

In a preferred embodiment the endoglucanase of the composition has at least 50%, such as at least 60%, 70%, 80% or even 90% homology to any of the aforementioned sequences.

In a preferred embodiment the xylanase GH family 10 of the composition is present in an amount of at least 20%, preferably at least 25%, such as at least 30%, at least 35%, at least 40%, at least 45% or even at least 50% w/w of the total xylanase and endoglucanase enzyme protein.

In a preferred embodiment the endoglucanase of GH Family 12, 7 and/or 5 endoglucanase of the composition is present in an amount of at least 25%, preferably 30%, such as at least 35%, at least 40%, at least 45% or even at least 50%, such as at least 55%, or even at least 60% w/w of the total xylanase and endoglucanase enzyme protein.

The composition according to the proceeding aspect may be used in a process comprising reducing the viscosity of an aqueous solution comprising a starch hydrolysate.

The composition may even be used in a process comprising filtering of an aqueous solution comprising a starch hydrolysate. In a preferred embodiment the aqueous solution comprising a starch hydrolysate is a mash for beer making, and in another preferred embodiment the aqueous solution comprising a starch hydrolysate is a feed composition.

The process of the invention may be applied in the mashing of any grist. According to the invention the grist may comprise any starch and/or sugar containing plant material derivable from any plant and plant part, including tubers, roots, stems, leaves and seeds. Preferably the grist comprises grain, such as grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from grain. Most preferably the grist comprises malted grain, such as barley malt. Preferably, at least 10%, or more preferably at least 15%, even more preferably at least 25%, or most preferably at least 35%, such as at least 50%, at least 75%, at least 90% or even 100% (w/w) of the grist of the wort is derived from malted grain.

For mashing of low malt grists the mashing enzymes may be exogenously supplied. The enzymes mostly used as starch degrading enzymes include pullulanases, alpha-amylases and amyloglucosidases. The use of starch degrading enzymes in mashing is well-known to the skilled person.

Adjunct comprising readily fermentable carbohydrates such as sugars or syrups may be added to the malt mash before, during or after the mashing process of the invention but is preferably added after the mashing process. A part of the adjunct may be treated with a protease and/or a endoglucanase, and/or heat treated before being added to the mash of the invention.

During the mashing process, starch extracted from the grist is gradually hydrolyzed into fermentable sugars and smaller dextrins. Preferably the mash is starch negative to iodine testing, before wort separation.

The application of the appropriate xylanase and endoglucanase activities in the process of the present invention results in efficient reduction of beta-glucan and arabino-xylan level facilitating wort separation, thus ensuring reduced cycle time, high extract recovery and clear wort.

The wort produced by the process of the first aspect of the invention may be fermented to produce a beer. Fermentation of the wort may include pitching the wort with a yeast slurry comprising fresh yeast, i.e. yeast not previously used for the invention or the yeast may be recycled yeast. The yeast applied may be any yeast suitable for beer brewing, especially yeasts selected from *Saccharomyces* spp. such as *S. cerevisiae* and *S. uvarum*, including natural or artificially produced variants of these organisms. The methods for fermentation of wort for production of beer are well known to the person skilled in the arts.

The process of the invention may include adding silica hydrogel to the fermented wort to increase the colloidal stability of the beer. The processes may further include adding kieselguhr to the fermented wort and filtering to render the beer bright. The beer produced by fermenting the wort of the invention may be any type of beer, e.g. ale, strong ale, stout, porter, lager, pilsner, bitter, export beer, malt liquor, happoushu, Iambic, barley wine, high-alcohol beer, low-alcohol beer, low-calorie beer or light beer.

The beer produced by the process of the invention may be distilled to recover ethanol, e.g. for whisky production. Contemplated are any kind of whisky (spelled "whiskey" in US and Ireland) include bourbon, Canadian whisky, Irish whiskey, rye, and scotch.

Xylanase

For the present purposes a xylanase is an enzyme classified as EC 3.2.1.8. The official name is endo-1,4-beta-xylanase. The systematic name is 1,4-beta-D-xylan xylanohydrolase. Other names may be used, such as endo-(1-4)-beta-xylanase; (1-4)-beta-xylan 4-xylanohydrolase; endo-1,4-xylanase; xylanase; beta-1,4-xylanase; endo-1,4-xylanase; endo-beta-1,4-xylanase; endo-1,4-beta-D-xylanase; 1,4-beta-xylan xylanohydrolase; beta-xylanase; beta-1,4-xylan xylanohydrolase; endo-1,4-beta-xylanase; beta-D-xylanase. The reaction catalysed is the endohydrolysis of 1,4-beta-D-xylosidic linkages in xylans.

While the xylanase to be used for the present invention may be of any origin including mammalian, plant or animal origin it is presently preferred that the xylanase is of microbial origin. In particular the xylanase may be one derivable from a filamentous fungus or a yeast.

Xylanases have been found in a number of fungal species, in particular species of *Aspergillus*, such as *A. niger, A. awamori, A. aculeatus* and *A. oryzae, Trichoderma*, such as *T. reesei* or *T. harzianum, Penicillium*, such as *P. camenbertii*, *Fusarium*, such as *F. oxysporum, Humicola*, such as *H. insolens*, and *Thermomyces lanuginosa*, such as *T. lanuginosa*. Xylanases have also been found in bacterial species, e.g. within the genus *Bacillus*, such as *B. pumilus*.

Preferably, according to the process of the invention the xylanase is derived from a filamentous fungus such as from *Aspergillus* sp., *Bacillus* sp., *Humicola* sp., *Myceliophotora* sp., *Poitrasia* sp. *Rhizomucor* sp. or *Trichoderma*.

Substrate specificity was shown to be a key parameter for the performance of xylanases in the process of the invention. A xylanase with optimum performance in the process of the invention seems to be an enzyme which binds rather strongly to soluble arabino-xylan and rather weakly to insoluble arabino-xylan. Preferably the xylanase to be used in the present invention is a xylanase which in the binding assay in the Methods description of this disclosure has a barley soluble/insoluble fibre binding ratio of at least 0.50, preferably at least 0.60, more preferably at least 0.70, such as 0.80, 0.90, 1.00, 1.10 or even at least 1.20.

A number of xylanases identified having these characteristics are members of the glucoside hydrolase family 10. Preferably the xylanase to be used in the present invention is a Glycoside Hydrolase Family 10 (GH10) xylanase, and most preferably the xylanase is a GH10 xylanase which is also a type A xylanase i.e. a xylanase which cleaves insoluble wheat arabinoxylan polymers close to branched residues leaving terminal substituted xylose oligosaccharides (please see the examples for a definition of type A and B). As the GH10 enzymes are able to go closer to the branched xylose units, they form smaller oligosaccharides than the GH11 xylanases.

Preferably the xylanase to be used in the present invention has a functional CBM, such as a CBM of family 1.

Preferably, according to the process of the invention the xylanase is selected from the list consisting of the xylanase from shown as, the xylanase from *Aspergillus aculeatus* shown as SEQ ID NO:8 (AA XYL I), the xylanase from *Aspergillus aculeatus* shown as SEQ ID NO:9 (AA XYL II), the xylanase from *Bacillus halodurans* shown as SWISS PROT P07528 (BH XYL A), the xylanase from *Humicola insolens* shown as SEQ ID NO:12 (HI XYL III), the xylanase from *Myceliophotora thermophila* shown as SEQ ID NO:13 (MT XYL I), and the xylanase from *Trichoderma reesei*, such as the xylanase shown as SEQ ID NO:17. Also preferred are any sequence having at least 50%, at least 60%, at least 70%, at least 80%, or even at least 90% homology to any of the aforementioned xylanase sequences.

Endoglucanase

For the present purposes an endoglucanase is an enzyme classified as EC 3.2.1.4. While the endoglucanase to be used for the present invention may be of any origin including mammalian, plant or animal origin it is presently preferred that the endoglucanase is of microbial origin. In particular the endoglucanase may be one derivable from a filamentous fungus or a yeast.

Preferably the endoglucanase is a Glycoside Hydrolase Family 12 (GH12), Glycoside Hydrolase Family 7 (GH7) or a Glycoside Hydrolase Family 5 (GH5) glucanase. More preferably the endoglucanase is a polypeptide having a beta-jelly-roll or a b8/a8-barrell in superstructure.

While the endoglucanase to be used for the present invention may be of any origin including mammalian, plant or animal origin it is presently preferred that the endoglucanase is of microbial origin. In particular the endoglucanase may be one derivable from a filamentous fungus or a yeast.

More preferably, according to the process of the invention the endoglucanase is derived from a filamentous fungus such as from *Aspergillus* sp. or *Humicola* sp.

Preferably, according to the process of the invention the endoglucanase is selected from the list consisting of the endoglucanase from *Aspergillus aculeatus* shown in SEQ ID NO:1 (AA EG I), the endoglucanase from *Aspergillus aculeatus* shown in SEQ ID NO:2 (AA EG II), the endoglucanase from *Aspergillus aculeatus* shown in SEQ ID NO:16 (AA EG III), the endoglucanase from *Humicola insolens* shown in SEQ ID NO:3 (HI EG I), the endoglucanase from *Humicola insolens* shown in SEQ ID NO:4 (HI EG III), the endoglucanase from *Humicola insolens* shown in SEQ ID NO:5 (HI EG IV), the endoglucanase from *Trichoderma* sp. shown in SEQ ID NO:18, the endoglucanase from *Trichoderma* sp. shown in SEQ ID NO:19 or the endoglucanase from *Trichoderma* sp. shown in SEQ ID NO:20. Also preferred are any sequence having at least 50%, at least 60%, at least 70%, at least 80%, or even at least 90% homology to any of the aforementioned sequences.

Other GH12 glucanases includes endoglucanases obtained from *Aspergillus* sp. such as from *Aspergillus kawachii* (SWISSPROT Q12679), or *Aspergillus niger* (SWISSPROT O74705), *Aspergillus oryzae* (SWISSPROT Q13454), from *Erwinia* sp., such as from *Erwinia carotovora* (SWISSPROT P16630), and from *Thermotoga* sp., such as from *Thermotoga maritima* (SWISSPROT Q60032 or Q9S5×8). Also preferred are any sequence having at least 50%, at least 60%, at least 70%, at least 80%, or even at least 90% homology to any of the aforementioned GH12 glucanases sequences.

Other GH7 glucanases includes endoglucanases obtained from *Agaricus* sp., such as from *Agaricus bisporus* (SWISSPROT Q92400), from *Aspergillus* sp., such as from *Aspergillus niger* (SWISSPROT Q9UVS8), from *Fusarium* sp., such as from *Fusarium oxysporum* (SWISSPROT P46238), from *Neurospora* sp., such as from *Neurospora crassa* (SWISSPROT P38676), and from *Trichoderma* sp., such as from *Trichoderma longibrachiatum* (SWISSPROT Q12714). Also preferred are any sequence having at least 50%, at least 60%, at least 70%, at least 80%, or even at least 90% homology to any of the aforementioned GH7 glucanases sequences.

Other GH5 glucanases includes endoglucanases obtained from *Acidothermus* sp., such as from *Acidothermus cellulolyticus* (SWISSPROT P54583), from *Aspergillus* sp., such as from *Aspergillus niger* (SWISSPROT O74706), and from *Bacillus* sp., such as from *Bacillus polymyxa* (SWISSPROT P23548). Also preferred are any sequence having at least 50%, at least 60%, at least 70%, at least 80%, or even at least 90% homology to any of the aforementioned GH5 glucanases sequences.

Arabinofuranosidase

Arabinofuranosidase EC 3.2.1.55, common name alpha-N-arabinofuranosidase hydrolysise terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans and arabinogalactans.

MATERIALS AND METHODS

Xylanase Activity

The xylanolytic activity can be expressed in FXU-units, determined at pH 6.0 with remazol-xylan (4-O-methyl-D-glucurono-D-xylan dyed with Remazol Brilliant Blue R, Fluka) as substrate.

A xylanase sample is incubated with the remazol-xylan substrate. The background of non-degraded dyed substrate is precipitated by ethanol. The remaining blue colour in the supernatant (as determined spectrophotometrically at 585 nm) is proportional to the xylanase activity, and the xylanase units are then determined relatively to an enzyme standard at standard reaction conditions, i.e. at 50.0° C., pH 6.0, and 30 minutes reaction time.

A folder AF 293.6/1 describing this analytical method in more detail is available upon request to Novozymes A/S, Denmark, which folder is hereby included by reference.

Glucanase Activity

The cellulytic activity may be measured in fungal endoglucanase units (FBG), determined on a 0.5% beta-glucan substrate at 30° C., pH 5.0 and reaction time 30 min. Fungal endoglucanase reacts with beta-glucan releases glucose or reducing carbohydrate which is determined as reducing sugar according to the Somogyi-Nelson method.

1 fungal endoglucanase unit (FBG) is the amount of enzyme which according to the above outlined standard conditions, releases glucose or reducing carbohydrate with a reduction capacity equivalent to 1 micromol glucose per minute.

Enzymes

Ultraflo® L, a multicomponent enzyme composition derived from *Humicola insolens* comprising a mixture of endoglucanases, xylanases, pentosanases and arabanases. Ultraflo® L is standardized to 45 FBG/g, and has a gravity of approximately 1.2 g/ml. Ultraflo® is available from Novozymes A/S.

Viscozyme® L, a multicomponent enzyme composition derived from *Aspergillus aculeatus* comprising a mixture of endoglucanases, arabanases and xylanases. Viscozyme® L is standardized to 100 FBG/g, and has a gravity of approximately 1.2 g/m I. Viscozyme is available from Novozymes A/S.

Alcalase®, Subtilisin a protease composition derived from *Bacillus licheniformis*. Alcalase® is available from Novozymes A/S.

Termamyl SC®, a *Bacillus* alpha-amylase available from Novozymes A/S.

The following monocomponent endoglucanases and xylanases were applied:

Endoglucanases;

| | | | |
|---|---|---|---|
| AA EG I | *Aspergillus aculeatus* | | SEQ ID NO: 1 |
| AA EG II | *Aspergillus aculeatus* | Cel12b | SEQ ID NO: 2 |
| AA EG III | *Aspergillus aculeatus* | Cel12a | SEQ ID NO: 16 |
| HI EG I | *Humicola insolens* | Cel12a, GH12 | SEQ ID NO: 3. |
| HI EG III | *Humicola insolens* | Cel12a, GH12 | SEQ ID NO: 4. |
| HI EG IV | *Humicola insolens* | Cel5a, GH12 | SEQ ID NO: 5 |
| HI EG V | *Humicola insolens* | Cel45a, GH45 | SEQ ID NO: 8 |
| TA EG | *Thermoascus aurantiacus* | | SEQ ID NO: 7 |
| BG025 | | | |

Xylanases

| | | | |
|---|---|---|---|
| AA XYL I | *Aspergillus aculeatus* | GH10, Type A | SEQ ID NO: 8 |
| AA XYL II | *Aspergillus aculeatus* | GH10, Type A | SEQ ID NO: 9 |
| AA XYL III | *Aspergillus aculeatus* | GH11, Type B | SEQ ID NO: 10 |
| BH XYL A | *Bacillus halodurans* | GH10, Type A | SWISS PROT P07528. |
| HI XYL I | *Humicola insolens* | GH11, Type B | SEQ ID NO: 11 |
| HI XYL III | *Humicola insolens* | GH10, Type A | SEQ ID NO: 12 |
| MT XYL I | *Myceliophotora thermophila* | GH10, Type A | SEQ ID NO: 13 |
| MT XYL III | *Myceliophotora thermophila* | GH11, Type B | SEQ ID NO: 14 |
| TL XYL | *Thermomyces lanuginosus* | GH11, Type B | SEQ ID NO: 15 |

Methods

Mash Preparation

Unless otherwise stated mashing was performed as follows. Except when noted (e.g. with regard to enzyme dosage) the mash was prepared according to EBC: 4.5.1 using malt grounded according to EBC: 1.1. Mashing trials were performed in 500 ml lidded vessels incubated in water bath with stirring and each containing a mash with 50 g grist and adjusted to a total weight of 300±0.2 g with water preheated to the initial incubation temperature +1° C. The wort produced was app. 12% Plato.

Mashing Temperature Profile

Unless otherwise stated mashing was carried out using an initial incubation temperature at 52° C. for 30 minutes, followed by an increasing step to 63° C. remaining here for 20 min. The profile is continued with an increasing step to 72° C. for 30 min, and mashing off at 78° C. for 5 min. All step wise temperature gradients are achieved by an increase of 1° C./min. The mash is cooled to 20° C. during 15 min, which result in a total incubation period of 2 hours and 11 min.

Additional Methods

Methods for analysis of raw products, wort, beer etc. can be found in Analytica-EBC, Analysis Committee of EBC, the European Brewing Convention (1998), Verlag Hans Carl Geranke-Fachverlag. For the present invention the methods applied for determination of the following parameters were as indicated below.

Plato: refractometer.

Beta-glucan: EBC: 8.13.2 (High Molecular weight beta-glucan content of wort:

Fluorimetric Method).

Turbidity: EBC: 4.7.1

Filterability: Volume of filtrate (ml) determination: According to EBC: 4.5.1 (Extract of Malt: Congress Mash) subsection 8.2. Filterability: Filtration volume is read after 1 hour of filtration through fluted filter paper, 320 mm diameter. Schleicher and Schüll No. 597 ½, Machery, Nagel and Co. in funnels, 200 mm diameter, fitted in 500 ml flasks.

Extract recovery: EBC: 4.5.1 (Extract of Malt: Congress Mash, Extract in dry). The term extract recovery in the wort is defined as the sum of soluble substances (glucose, sucrose, maltose, maltotriose, dextrins, protein, gums, inorganic, other substances) extracted from the grist (malt and adjuncts) expressed in percentage based on dry matter. The remaining insoluble part is defined as spent grains.

a) $E_1 = \dfrac{P(M + 800)}{100 - P}$ b) $E_2 = \dfrac{E_1 \cdot 100}{100 - M}$ where;

$E_1$=the extract content of sample, in % (m/m)

$E_2$=the extract content of dry grist, in % (m/m)

P=the extract content in wort, in % Plato

M=the moisture content of the grist, in % (m/m)

800=the amount of destilled water added into the mash to 100 g of grist

Viscosity: Automated Microviscometer (AMVn) is based on the rolling ball principle. The sample to be measured is introduced into a glass capillary in which a steel ball rolls. The viscous properties of the test fluid can be determined by measuring the rolling time of the steel ball. The rolling time $t_0$ of a ball over a defined measuring distance in a capillary is measured. The dynamic viscosity $\eta$ of the sample is calculated from the calibration constant $K_1(\alpha)$ of the measuring system, the rolling time $t_0$ and the difference of density $\Delta\rho$ between the ball and the sample. The following equation is used:

$\eta = K_1(\alpha) \cdot t_0 \cdot (\rho_k - \rho_s)$, where $\eta$=Dynamic viscosity of the sample, [mPa·s]

$K(\alpha)$=Calibration constant for the Measuring system [mPa·scm³/g]

$t_0$=Rolling time for 100 mm [s]

$\rho_k$=Ball density [7,85 g/cm³]

$\rho_s$=Density of the sample measured [g/cm³]

The viscosity is presented based on the extract)(Plato° as is, or converted to 8,6° Plato based upon a Congress mashing procedure.

EXAMPLE 1

Characterisation of Xylanases Using Binding Assay

Production of Fibre Fractions

Soluble fibre fraction of barley was produced as follows:
1. 50 kg of barley was milled and slurred into 450 kg water at 50° C. under stirring.
2. The extraction was carried out for 30 minutes under stirring.
3. Using a preheated decanter centrifuge at 50° C., and a solids ejecting centrifuge a particle free and clarified fraction was prepared.
4. The clarified fraction was ultra filtered at 50° C. on a tubular membrane with a cut-off value of 20000 Dalton. The ultra filtration process was continued until the viscosity increased and the flow was reduced significantly in the system.
5. The concentrated fraction was collected and lyophilized.

Insoluble fibre fraction of barley was produced as follows:
1. 50 kg of barley was milled and slurred into 450 kg of water at 50° C. 0.25 kg of Termamyl SC was added and the solution was heated to 85° C. under stirring. The reaction was carried out for 30 minutes. A sample was taken for starch analysis by iodine test.
2. The sample was centrifuged for 5 min at 3000×g (in 10 ml centrifuge vial). ° Plato was measured by using a refractometer on the supernatant. Starch conversion was followed by iodine colour reaction; if blue starch was remaining.
3. The reaction was continued until ° Plato has stabilized. The reaction product was ready for centrifugation.
4. The centrifugation was carried out using a decanter. The separation was carried out at 75° C., and a clear and particle free supernatant was obtained. This fraction was discarded. Only the solid fraction was used in the following process.
5. The collected solid fraction was slurred into 500 kg of hot water. The temperature of this slurry was adjusted to 50° C.
6. pH was adjusted to 7.5 using NaOH. A hydrolysis reaction was carried out using 125 g Alcalase 2.4 L. During the hydrolysis pH was maintained at pH=7.5 (pH-stat) and the reaction time was 120 minutes. Hereafter the reaction was left stirred without pH-stat at T=50° C. over night.
7. pH was then adjusted to 6.5 using HCl.
8. The reaction mixture was centrifuged using the decanter.
9. The solid fraction was collected and washed with 500 L of water at 50° C. for 30 minutes. The centrifugation step and washing step was repeated.
10. This washed solid fraction was lyophilized.

Fibre Fraction Analysis

The sugar composition of the fibre fractions was analysed as follows: 1 g of fibre was added 50 mL of 1 M HCl and incubated at 100° C. for 2 hours with shaking. After this treatment the reaction mixture was immediately cooled on ice and 11 mL of 4 M NaOH was added to neutralise the mixture. The content of arabinose, galactose, glucose and xylose was quantified using a Dionex BioLC system equipped with a CarBoPac PA-1 column as described in Sørensen et al. (2003) Biotech. Bioeng. vol. 81, No. 6, p. 726-731. The results are shown in table 1.

TABLE 1

Content (g/kg) of the individual sugars in the fibre fractions from barley

|  | Arabinose | Galactose | Glucose | Xylose |
|---|---|---|---|---|
| Soluble fibers | 34.9 | 14.8 | 486.6 | 38.1 |
| Insoluble fibers | 102.3 | 10.4 | 42.3 | 207.2 |

Xylanases Binding Assay

The xylanases binding assay was performed as follows: The fibre (10 mg) was washed in an Eppendorf tube by whirly-mixing with 500 microL of acetate buffer (50 mM, pH 5.5, 0.1% Triton X-100) before being centrifuged for 2 min at 13000 g. Washing and centrifuging was performed twice. The solution containing the enzyme* (500 microL, in acetate buffer pH 5.5) was then added to the substrate and the mixture was thoroughly whirly-mixed and kept in an ice bath for 10 min. The Eppendorf tube containing the reaction mixture was then centrifuged at 14000 g for 3 min where after initial and residual activity was determined by using as substrate 0.2% AZCL-Arabinoxylan from wheat (Megazyme) in 0.2 M Na-phosphate buffer pH 6.0+0.01% Triton-x-100. A vial with 900 microL substrate was preheated to 37° C. in a thermo-mixer. 100 microL enzyme sample was added followed by incubation for 15 min at 37° C. and maximum shaking. The vial was placed on ice for 2 min before being centrifuged for 1 min at 20.000 g. From the supernatant 2×200 microL was transferred to a microtiter plate and endpoint OD 590 nm was measured and compared relative to a control. The control was 100 microL enzyme sample incubated with 900 microL 0.2 M Na-phosphate buffer pH 6.0+0.01% Triton-x-100 instead of substrate and subsequently all activity is recovered in the supernatant and this value set to 1. The results are shown in table 2.

The two xylanases having the highest soluble/insoluble barley fibre binding ratio, Xylanase II and I from *A. aculeatus*, were also the two xylanases having the best performance in the mashing trials.

TABLE 2

Soluble/insoluble barley fibre binding ratio. Relative activity measured in the supernatant after 10 min incubation with soluble and insoluble barley fibre fractions and the resulting ratios between activities measured in the supernatants over soluble and insoluble barley fibre.

| Xylanase | GH Family | Insoluble barley fibers | Soluble barley fibers | Ratio Soluble/ |
|---|---|---|---|---|
| Aspergillus aculeatus Xyl II | 10 | 86 | 104 | 1.21 |
| Aspergillus aculeatus Xyl I | 10 | 105 | 56 | 0.52 |
| Humicola insolens Xyl II | 11 | 82 | 37 | 0.45 |
| Thermomyces lanuginosus Xyl | 11 | 83 | 14 | 0.17 |
| Humicola insolens Xyl I | 11 | 74 | 7 | 0.09 |
| Bacillus halodurans Xyl A | 11 | 79 | 7 | 0.09 |

EXAMPLE 2

Characterization of Xylanase Specificity

High field Nuclear Magnetic Resonance ($^1$H NMR) was applied to identify differences in xylanase specificity towards insoluble wheat arabinoxylan (AX) (insoluble, Megazyme). In $^1$H NMR, arabinoxylan or oligosaccharides hereof (AXO) show signals (chemical shifts) around 5.0-5.5 ppm arising from the anomeric protons H-1 from the α-L-arabinofuranoside units. The individual differences among these depending on their local surroundings can be used to evaluate the specificity of xylanases towards this highly branched polymer. The standard condition was 10 mg/mL of AX in 50 mM acetate buffer, pH 5.5 was incubated with 0.1 XU/mL for 120 min at 30° C. The xylanase was then inactivated (95° C., 20 min) and the solution concentrated on a rotary evaporator. The sample was then evaporated twice from $D_2O$ (1 mL) and finally re-suspended in $D_2O$ (~0.8 mL) before being analyzed. $^1$H NMR spectra were recorded on a Varian Mercury 400 MHz at 30° C. Data were collected over 100 scans and the HDO signal was used as a reference signal (4.67 ppm).

Degradation of AX with a xylanase changes the $^1$H NMR spectra according to the specificity of the enzyme. Thus, the chemical shift of the arabinofuranoside H-1 changes if the arabinose in the resulting oligosaccharide is located on a terminal xylose as compared to an "internal" xylose. This will be the result if the xylanase is capable at placing a substituted xylose unit in its +1 subsite. Using the applied conditions it was found that all tested GH10 xylanases was able to do this, whereas no GH11 xylanases having the characteristic were found. Type A refers to a xylanase that cleaves next to branched residues (leaving terminal substituted xylose oligosaccharides) whereas Type B refers to a xylanase that cleaves between unsubstituted xylose units giving internal substituted units only. Type A xylanases are also capable at cleaving between unsubstituted xylose units. Examples of Type A and Type B xylanase identified by the inventors are shown in table 3. For the invention a type A xylanase is preferred.

TABLE 3

Examples of Type A and Type B xylanases

| Type A | Type B |
|---|---|
| Aspergillus aculeatus Xyl I | Biobake (Quest) |
| Aspergillus aculeatus Xyl II | Humicola insolens Xyl I |
| Bacillus halodurans Xyl A | Myceliophotora thermophila Xyl III |
| Humicola insolens Xyl III | Thermomyces lanuginosus Xyl I |
| Myceliophotora thermophila Xyl I | |

Even within the type A xylanases the preference for cleavage next to branched residues or between unsubstituted xylose varies as shown in table 4, where the ratio $I_{1,3terminal}/I_{1,3internal}$ relates to the ratio between the respective integrals of the two types of protons. Thus, type A cleavage result in an increase of $I_{1,3terminal}$ whereas type B does not. The chemical shifts for the two types of protons are: 1,3-linked arabinofuranoside H-1 on terminal xylose: 5.26 ppm and 1,3-linked arabinofuranoside H-1 on internal xylose: 5.32 ppm. For the invention a type A xylanase having a $I_{1,3terminal}/I_{1,3internal}$ ratio of at least 0.25, such as at least 0.30, al least 0.40, at least 0.50, or even at least 0.60, is preferred.

TABLE 4

Xylanases specificity, preference for cleavage next to branched residues or between unsubstituted xylose

| | $I_{1,3terminal}/I_{1,3internal}$ |
|---|---|
| *Myceliophotora thermophila* Xyl I | 0.64 |
| *Aspergillus aculeatus* Xyl II | 0.60 |
| *Humicola insolens* Xyl III | 0.30 |
| *Aspergillus aculeatus* Xyl I | 0.28 |

EXAMPLE 3

Characterization of endoglucanase specificity

Specificity of endoglucanases was studied by analyzing degradation products upon incubation with barley beta-glucan. Eppendorf tubes with 0.1 and 10 microgram/ml purified enzyme and 5 mg/ml barley beta-glucan (Megazyme, low viscosity) in 50 mM sodium acetate, 0.01% Triton X-100 at pH 5.5 were incubated in an Eppendorf thermomixer at 50° C. with agitation.

Enzymes tested were endoglucanase EG I from *Humicola insolens*, endoglucanase EG III from *Humicola insolens*, endoglucanase *Humicola insolens* EG IV, *Aspergillus aculeatus* EG II (XG5, Cel12B), and *Aspergillus aculeatus* EG III (XG53, Cel12A).

Samples were withdrawn between 1 and 21.5 hours and inactivated by heating for 30 min at 95° C. Half the volume of each sample was degraded with lichenase (0.085 microgram/ml, Megazyme, from *Bacillus subtilis*) in 50 mM MES, 1 mM CaCl2, pH 6.5 for 2 hours at 50° C., after which the lichenase was inactivated by heating to 95° C. for 30 min. Samples with and without lichenase treatment were diluted appropriately with Milli Q water and analyzed on a Dionex DX-500 HPAEC-PAD system (CarboPac PA-100 column; A buffer: 150 mM NaOH; B buffer: 150 mM NaOH+0.6 M sodium acetate; Flow rate: 1 ml/min. Elution conditions: 0-3 min: 95% A+5% B; 3-19 min: linear gradient: 95% A+5% B to 50% A and 50% B; 19-21 min: linear gradient: 50% A+50% B to 100% B; 21-23 min: 100% B). As reference on the Dionex system a mixture of cellooligosaccharides was used (DP1 to DP6, 100 microM of each). Peaks in chromatograms were identified using the cellooligo references and known composition of barley beta-glucan after lichenase treatment (e.g. lzydorczyk, M. S., Macri, L. J., & MacGregor, A. W., 1997, Carbohydrate Polymers, 35, 249-258). Quantification of peaks in chromatograms was done using response factors obtained for cellooligo references and assuming that response factor was identical for oligosaccharides of same DP with beta-1,3 bonds. For oligosaccharides larger than DP6 response factor of DP6 was used.

From the analysis of degradation products with EG I from *Humicola insolens* (Tables 5 and 6), it was found that the enzyme is able to degrade both beta-1,3 and beta-1,4 bonds. Initially, cellobiose, cellotriose and to some extent laminaribiose are the main products increasing after lichenase treatment. This indicates that beta-1,3 bonds are accepted between glucose units in subsites −4/−3, −5/−4 and +1/+2. The main products with highest enzyme dosage (10 microgram/ml) and longest incubation time (21.5 hours) were found to be glucose and cellobiose.

With EG III from *Humicola insolens* (Tables 7 and 8) the main products after 21.5 hours and 10 microgram/ml enzyme were tetraoses (mainly Glu(beta-1,4)Glu(beta-1,3)Glu(beta-1,4)Glu and Glu(beta-1,4)Glu(beta-1,4)Glu(beta-1,3)Glu but not Glu(beta-1,3)Glu(beta-1,4)Glu(beta-1,4)Glu), pentaoses (probably mainly Glu(beta-1,3)Glu(beta-1,4)Glu(beta-1,4)Glu(beta-1,3)Glu and Glu(beta-1,4)Glu(beta-1,4)Glu(beta-1,3)Glu(beta-1,4)Glu) and larger oligomers. Composition of degradation products after lichenase treatment shows that the enzyme exclusively degrades the beta-1,4 bonds in beta-glucan. Furthermore, the beta-1,4 linkages that are hydrolysed are mainly those not hydrolysed by lichenases (without adjacent beta-1,3 bond towards the non-reducing end). That the amount of Glu(beta-1,4)Glu(beta-1,3)Glu ("Lic3") after lichenase treatment does not decrease significantly even after 21.5 hours with 10 microgram/ml indicates that the enzyme only has limited activity on stretches with only two beta-1,4 bonds between beta-1,3 linkages. The appearance of significant amounts of glucose and laminaribiose but not cellobiose or cellotriose after lichenase treatment indicates that beta-1,3 bonds are accepted between glucose units in subsites −3/−2 and +1/+2 but not between −4/−3 or −5/−4.

The enzyme EG IV from *Humicola insolens* mainly degrades the beta-glucan to larger oligomers (Tables 9 and 10), but after 21.5 hours with 10 microgram/ml enzyme substantial amounts of cellobiose and oligomers of DP4 (probably mainly Glu(beta-1,4)Glu(beta-1,3)Glu(beta-1,4)Glu and Glu(beta-1,3)Glu(beta-1,4)Glu(beta-1,4)Glu) are formed. The enzyme degrades about equal amounts of beta-1,4 and beta-1,3 bonds in beta-glucan and the beta-1,4 bonds cleaved seem to be those without an adjacent beta-1,3 bond towards the non-reducing end (unlike lichenases). Lichenase treatment gives increased cellotriose already after limited hydrolysis with EG IV, whereas cellobiose and glucose only appear after more extensive hydrolysis with EG IV. This indicates that beta-1,3 bonds are better accepted between glucose in subsites −5/−4 than between −4/−3 and especially −3/−2. The appearance of laminaribiose after lichenase treatment shows that beta-1,3 bonds are also accepted between glucose in subsites +1/+2.

With *Aspergillus aculeatus* EGII (XG5, Cel12B), glucose is seen to be the main low molecular weight product (Tables 11 and 12). Lichenase treatment of samples with little degradation of beta-glucan by EG II gives increase of cellobiose, cellotriose and laminaribiose but not glucose. This indicates that beta-1,3 bonds are accepted between glucose units in subsites −5/−4, −4/−3 and +1/+2 but probably not −3/−2. Thus, the glucose liberated by EG II is probably released by exo-action on degradation products. The enzyme is able to hydrolyse both beta-1,4 and beta-1,3 bonds although beta-1,4 linkages seem to be preferred. After 20 hours with the highest enzyme concentration, the beta-glucan is seen to be almost totally degraded to glucose.

The *Aspergillus aculeatus* EG III (XG53, Cel12A) rapidly degrades the beta-glucan giving oligomers of DP4 (mainly Glu(beta-1,3)Glu(beta-1,4)Glu(beta-1,4)Glu and Glu(beta-1,3)Glu(beta-1,4)Glu(beta-1,4)Glu) and DP5 (mainly Glu (beta-1,4)Glu(beta-1,4)Glu(beta-1,3)Glu(beta-1,4)Glu but also some Glu(beta-1,4)Glu(beta-1,3)Glu(beta-1,4)Glu (beta-1,4)Glu and Glu(beta-1,4)Glu(beta-1,4)Glu(beta-1,4)Glu(beta-1,3)Glu) (Tables 13 and 14). After 20 hours with the highest enzyme concentration significant amounts of cellobiose, glucose and cellotriose are also formed. Lichenase treatment of samples gives increase of glucose, cellotriose and laminaribiose and especially cellobiose. This indicates that beta-1,3 bonds may be preferred between glucose units in subsites −4/−3 but are also accepted between −5/−4, −3/−2 and +1/+2. The enzyme is capable of degrading both beta-1,4 and beta-1,3 linkages.

TABLE 5

Degradation products of barley beta-glucan with endoglucanase *Humicola insolens* EG I given as weight % of degradation products.

| | Enzyme dosage (microgram/ml) | | | | | |
|---|---|---|---|---|---|---|
| | 0.1 | 0.1 | 0.1 | 10 | 10 | 10 |
| | Incubation time (hours) | | | | | |
| | 1 | 2.5 | 21.5 | 1 | 2.5 | 21.5 |
| Glu | 0.10 | 0.28 | 0.35 | 3.68 | 15.45 | 40.96 |
| $Cel_2$ | 0.40 | 0.93 | 1.51 | 13.80 | 27.32 | 28.76 |
| $Cel_3$ | 0.69 | 1.64 | 2.38 | 9.91 | 6.00 | 0.00 |
| $Cel_4$ | 0.25 | 0.48 | 0.68 | 2.37 | 0.85 | 0.00 |
| $Cel_5$ | 0.00 | 0.40 | 0.35 | 1.66 | 0.11 | 0.00 |
| $Cel_6$ | 0.00 | 0.00 | 0.00 | 0.00 | 0.00 | 0.00 |
| $Lam_2$ | 0.00 | 0.00 | 0.13 | 0.07 | 0.06 | 2.12 |
| $DP_3$ | 0.63 | 0.00 | 0.06 | 0.86 | 3.51 | 5.33 |
| $DP_4$ | 0.00 | 0.00 | 0.08 | 1.29 | 4.40 | 4.13 |
| $DP_5$ | 0.87 | 2.38 | 3.65 | 22.91 | 23.44 | 9.14 |
| $DP_6$ | 1.12 | 2.66 | 4.50 | 16.08 | 4.16 | 3.41 |
| DP > 6 | 95.93 | 91.23 | 86.30 | 27.38 | 14.70 | 6.16 |

Glu: Glucose.
$Cel_i$: Cellooligo of DP i.
$Lam_2$: Laminaribiose.
$DP_i$: Oligosaccharide of DP i with a single beta-1,3 bond and the rest beta-1,4 bonds between the glucose units.
DP > 6: Oligosaccharide consisting of more than 6 glucose units.

TABLE 6

Degradation products of barley beta-glucan with endoglucanase *Humicola insolens* EG I and subsequent lichenase degradation given as weight % of degradation products.

| | Enzyme dosage (microgram/ml) | | | | | |
|---|---|---|---|---|---|---|
| | 0.1 | 0.1 | 0.1 | 10 | 10 | 10 |
| | Incubation time (hours) | | | | | |
| | 1 | 2.5 | 21.5 | 1 | 2.5 | 21.5 |
| Glu | 0.14 | 0.17 | 0.45 | 5.15 | 16.24 | 43.66 |
| $Cel_2$ | 3.38 | 4.99 | 10.09 | 36.73 | 43.18 | 35.48 |
| $Cel_3$ | 1.24 | 3.31 | 5.26 | 14.14 | 6.42 | 0.17 |
| $Cel_4$ | 0.21 | 0.79 | 1.39 | 3.79 | 0.90 | 0.00 |
| $Cel_5$ | 0.00 | 0.16 | 0.62 | 1.18 | 0.84 | 0.00 |
| $Cel_6$ | 0.00 | 0.00 | 0.00 | 0.00 | 0.00 | 0.00 |
| $Lam_2$ | 2.95 | 2.43 | 3.58 | 9.90 | 7.53 | 4.99 |
| $DP_3$ | 61.59 | 58.54 | 52.42 | 3.56 | 6.49 | 5.46 |
| $DP_4$ | 20.92 | 19.72 | 16.97 | 5.19 | 6.01 | 4.58 |
| $DP_5$ | 4.33 | 4.10 | 5.46 | 13.49 | 9.44 | 2.84 |
| $DP_6$ | 2.23 | 2.88 | 2.75 | 4.84 | 1.00 | 2.47 |
| DP > 6 | 3.01 | 2.91 | 0.29 | 2.04 | 1.96 | 0.34 |

Glu: Glucose.
$Cel_i$: Cellooligo of DP i.
$Lam_2$: Laminaribiose.
$DP_i$: Oligosaccharide of DP i with a single beta-1,3 bond and the rest beta-1,4 bonds between the glucose units.
DP > 6: Oligosaccharide consisting of more than 6 glucose units.

TABLE 7

Results upon degradation of barley beta-glucan with endoglucanase *Humicola insolens* EG III given as weight % of degradation products.

| | Enzyme dosage (microgram/ml) | | | | | |
|---|---|---|---|---|---|---|
| | 0.1 | 0.1 | 0.1 | 10 | 10 | 10 |
| | Incubation time (hours) | | | | | |
| | 1 | 2.5 | 21.5 | 1 | 2.5 | 21.5 |
| Glu | 0.00 | 0.08 | 0.06 | 0.30 | 0.25 | 0.68 |
| Cel2 | 0.00 | 0.00 | 0.00 | 0.08 | 0.01 | 0.53 |
| Cel3 | 0.00 | 0.00 | 0.00 | 0.00 | 0.00 | 0.00 |
| Cel4 | 0.00 | 0.00 | 0.00 | 0.00 | 0.03 | 0.00 |
| Cel5 | 0.00 | 0.00 | 0.00 | 0.00 | 0.00 | 0.00 |
| Cel6 | 0.00 | 0.00 | 0.00 | 0.00 | 0.00 | 0.00 |
| Lam2 | 0.00 | 0.00 | 0.00 | 0.00 | 0.03 | 0.24 |
| DP3 | 1.07 | 0.00 | 0.00 | 0.66 | 0.05 | 0.00 |
| DP4 | 0.00 | 0.14 | 0.53 | 5.99 | 7.95 | 39.08 |
| DP5 | 0.78 | 0.00 | 0.75 | 4.50 | 6.68 | 25.08 |
| DP6 | 0.00 | 0.00 | 0.36 | 1.26 | 1.92 | 7.08 |
| DP > 6 | 98.15 | 99.78 | 98.29 | 87.22 | 83.09 | 27.31 |

Glu: Glucose.
$Cel_i$: Cellooligo of DP i.
$Lam_2$: Laminaribiose.
$DP_i$: Oligosaccharide of DP i with a single beta-1,3 bond and the rest beta-1,4 bonds between the glucose units.
DP > 6: Oligosaccharide consisting of more than 6 glucose units.

TABLE 8

Results upon degradation of barley beta-glucan with endoglucanase *Humicola insolens* EG III and subsequent lichenase degradation given as weight % of degradation products.

| | Enzyme dosage (microgram/ml) | | | | | |
|---|---|---|---|---|---|---|
| | 0.1 | 0.1 | 0.1 | 10 | 10 | 10 |
| | Incubation time (hours) | | | | | |
| | 1 | 2.5 | 21.5 | 1 | 2.5 | 21.5 |
| Glu | 0.15 | 0.29 | 1.37 | 6.70 | 14.43 | 13.80 |
| Cel2 | 0.32 | 0.19 | 0.44 | 0.21 | 0.24 | 0.90 |
| Cel3 | 1.03 | 0.00 | 2.01 | 0.93 | 0.45 | 0.15 |
| Cel4 | 0.00 | 0.00 | 0.00 | 0.00 | 0.03 | 0.00 |
| Cel5 | 0.80 | 0.00 | 0.00 | 0.00 | 0.00 | 0.00 |
| Cel6 | 0.00 | 0.00 | 0.00 | 0.00 | 0.00 | 0.00 |
| Lam2 | 4.10 | 1.26 | 2.10 | 7.43 | 13.20 | 13.77 |
| "Lic3" | 59.81 | 65.09 | 61.00 | 47.76 | 40.48 | 56.20 |
| "Lic4" | 22.63 | 23.12 | 21.54 | 18.78 | 7.08 | 9.72 |
| "Lic5" | 4.24 | 4.45 | 4.92 | 10.59 | 15.64 | 2.88 |
| "Lic6" | 3.91 | 2.82 | 3.67 | 3.28 | 2.90 | 2.05 |
| "Lic7" | 3.00 | 2.79 | 2.93 | 4.32 | 5.54 | 0.55 |

Glu: Glucose.
$Cel_i$: Cellooligo of DP i.
$Lam_2$: Laminaribiose.
$DP_i$: Oligosaccharide of DP i with a single beta-1,3 bond and the rest beta-1,4 bonds between the glucose units.
DP > 6: Oligosaccharide consisting of more than 6 glucose units.

TABLE 9

Degradation products of barley beta-glucan with endoglucanase *Humicola insolens* EG IV given as weight % of degradation products. Glu: Glucose.

| | Enzyme dosage (microgram/ml) | | | | | |
|---|---|---|---|---|---|---|
| | 0.1 | 0.1 | 0.1 | 10 | 10 | 10 |
| | Incubation time (hours) | | | | | |
| | 1 | 2.5 | 21.5 | 1 | 2.5 | 21.5 |
| Glu | 0.00 | 0.00 | 0.00 | 0.13 | 0.63 | 0.66 |
| $Cel_2$ | 0.14 | 0.38 | 1.07 | 7.02 | 5.51 | 12.11 |
| $Cel_3$ | 0.09 | 0.19 | 0.77 | 2.89 | 1.72 | 1.02 |

TABLE 9-continued

Degradation products of barley beta-glucan with endoglucanase *Humicola insolens* EG IV given as weight % of degradation products. Glu: Glucose.

| | Enzyme dosage (microgram/ml) | | | | | |
|---|---|---|---|---|---|---|
| | 0.1 | 0.1 | 0.1 | 10 | 10 | 10 |
| | Incubation time (hours) | | | | | |
| | 1 | 2.5 | 21.5 | 1 | 2.5 | 21.5 |
| $Cel_4$ | 0.81 | 0.20 | 0.34 | 1.10 | 0.55 | 0.13 |
| $Cel_5$ | 0.15 | 0.28 | 0.30 | 0.00 | 0.00 | 0.00 |
| $Cel_6$ | 0.00 | 0.29 | 0.00 | 0.00 | 0.00 | 0.00 |
| $Lam_2$ | 0.00 | 0.00 | 0.00 | 0.00 | 0.04 | 0.16 |
| $DP_3$ | 0.00 | 0.00 | 0.00 | 0.68 | 0.00 | 0.11 |
| $DP_4$ | 0.00 | 0.00 | 0.00 | 1.03 | 1.83 | 12.77 |
| $DP_5$ | 0.18 | 0.21 | 0.07 | 0.59 | 0.71 | 3.25 |
| $DP_6$ | 0.00 | 0.13 | 0.26 | 5.78 | 6.04 | 2.44 |
| DP > 6 | 98.63 | 98.32 | 97.20 | 80.77 | 82.96 | 67.36 |

Celi: Cellooligo of DP i.
Lam2: Laminaribiose.
DPi: Oligosaccharide of DP i with a single beta-1,3 bond and the rest beta-1,4 bonds between the glucose units.
DP > 6: Oligosaccharide consisting of more than 6 glucose units.

TABLE 10

Degradation products of barley beta-glucan with endoglucanase *Humicola insolens* EG IV and subsequent lichenase degradation given as weight % of degradation products.

| | Enzyme dosage (microgram/ml) | | | | | |
|---|---|---|---|---|---|---|
| | 0.1 | 0.1 | 0.1 | 10 | 10 | 10 |
| | Incubation time (hours) | | | | | |
| | 1 | 2.5 | 21.5 | 1 | 2.5 | 21.5 |
| Glu | 0.07 | 0.05 | 0.09 | 1.83 | 2.93 | 7.24 |
| $Cel_2$ | 0.40 | 0.50 | 1.97 | 4.53 | 7.23 | 19.84 |
| $Cel_3$ | 1.45 | 2.05 | 5.59 | 11.84 | 12.00 | 6.94 |
| $Cel_4$ | 0.81 | 1.13 | 1.90 | 1.48 | 0.57 | 0.08 |
| $Cel_5$ | 0.00 | 0.00 | 0.00 | 0.00 | 0.00 | 0.00 |
| $Cel_6$ | 0.00 | 0.00 | 0.00 | 0.00 | 0.00 | 0.00 |
| $Lam_2$ | 2.10 | 3.92 | 3.82 | 5.43 | 7.41 | 11.87 |
| $DP_3$ | 63.45 | 61.92 | 60.26 | 54.03 | 47.65 | 30.59 |
| $DP_4$ | 22.95 | 23.32 | 21.96 | 16.11 | 11.03 | 15.88 |
| $DP_5$ | 4.97 | 4.99 | 3.46 | 3.03 | 2.51 | 4.01 |
| $DP_6$ | 3.82 | 0.20 | 0.49 | 0.11 | 3.04 | 1.00 |
| DP > 6 | 0.00 | 1.93 | 0.47 | 1.60 | 5.62 | 2.55 |

Celi: Cellooligo of DP i.
Lam2: Laminaribiose.
DPi: Oligosaccharide of DP i with a single beta-1,3 bond and the rest beta-1,4 bonds between the glucose units.
DP > 6: Oligosaccharide consisting of more than 6 glucose units.

TABLE 11

Degradation products of barley beta-glucan with endoglucanase *Aspergillus aculeatus* EG II (XG5, Cel12B) given as weight % of degradation products.

| | Enzyme dosage (microgram/ml) | | | |
|---|---|---|---|---|
| | 0.16 | 0.16 | 16 | 16 |
| | Incubation time (hours) | | | |
| | 1 | 20 | 1 | 20 |
| Glu | 0.17 | 2.30 | 33.64 | 99.25 |
| $Cel_2$ | 0.00 | 0.00 | 0.54 | 0.00 |
| $Cel_3$ | 0.00 | 0.00 | 0.60 | 0.00 |
| $Cel_4$ | 0.00 | 0.00 | 0.52 | 0.00 |
| $Cel_5$ | 0.00 | 0.00 | 0.11 | 0.00 |

TABLE 11-continued

Degradation products of barley beta-glucan with endoglucanase *Aspergillus aculeatus* EG II (XG5, Cel12B) given as weight % of degradation products.

| | Enzyme dosage (microgram/ml) | | | |
|---|---|---|---|---|
| | 0.16 | 0.16 | 16 | 16 |
| | Incubation time (hours) | | | |
| | 1 | 20 | 1 | 20 |
| $Cel_6$ | 0.00 | 0.00 | 0.00 | 0.00 |
| $Lam_2$ | 0.00 | 0.12 | 2.97 | 0.00 |
| $DP_3$ | 0.00 | 0.45 | 0.09 | 0.16 |
| $DP_4$ | 0.00 | 0.06 | 1.85 | 0.02 |
| $DP_5$ | 0.00 | 0.20 | 1.69 | 0.16 |
| $DP_6$ | 0.00 | 0.28 | 4.58 | 0.00 |
| DP >6 | 99.83 | 96.59 | 53.42 | 0.41 |

Glu: Glucose.
Celi: Cellooligo of DP i.
Lam2: Laminaribiose.
DPi: Oligosaccharide of DP i with a single beta-1,3 bond and the rest beta-1,4 bonds between the glucose units.
DP >6: Oligosaccharide consisting of more than 6 glucose units.

TABLE 12

Degradation products of barley beta-glucan with endoglucanase *Aspergillus aculeatus* EG II (XG5, Cel12B) and subsequent lichenase degradation given as weight % of degradation products.

| | Enzyme dosage (microgram/ml) | | | |
|---|---|---|---|---|
| | 0.016 | 0.016 | 1.6 | 1.6 |
| | Incubation time (hours) | | | |
| | 1 | 20 | 1 | 20 |
| Glu | 0.20 | 2.21 | 26.22 | 99.53 |
| $Cel_2$ | 4.88 | 0.61 | 1.31 | 0.00 |
| $Cel_3$ | 3.76 | 3.44 | 4.10 | 0.00 |
| $Cel_4$ | 0.00 | 0.20 | 0.82 | 0.00 |
| $Cel_5$ | 0.00 | 0.88 | 0.00 | 0.00 |
| $Cel_6$ | 0.00 | 0.00 | 0.00 | 0.00 |
| $Lam_2$ | 0.17 | 2.17 | 9.95 | 0.00 |
| $DP_3$ | 61.15 | 59.72 | 36.11 | 0.27 |
| $DP_4$ | 23.43 | 21.49 | 14.35 | 0.04 |
| $DP_5$ | 3.82 | 3.83 | 3.38 | 0.16 |
| $DP_6$ | 0.08 | 2.52 | 2.20 | 0.00 |
| DP >6 | 2.51 | 2.94 | 1.55 | 0.00 |

Glu: Glucose.
Celi: Cellooligo of DP i.
Lam2: Laminaribiose.
DPi: Oligosaccharide of DP i with a single beta-1,3 bond and the rest beta-1,4 bonds between the glucose units.
DP >6: Oligosaccharide consisting of more than 6 glucose units.

TABLE 13

Degradation products of barley beta-glucan with endoglucanase *Aspergillus aculeatus* EG III (XG53, Cel12A) given as weight % of degradation products.

| | Enzyme dosage (microgram/ml) | | | |
|---|---|---|---|---|
| | 0.1 | 0.1 | 10 | 10 |
| | Incubation time (hours) | | | |
| | 1 | 20 | 1 | 20 |
| Glu | 0.05 | 0.23 | 1.42 | 13.28 |
| $Cel_2$ | 0.09 | 0.78 | 4.20 | 20.68 |
| $Cel_3$ | 0.15 | 1.21 | 2.69 | 7.57 |

TABLE 13-continued

Degradation products of barley beta-glucan with endoglucanase
*Aspergillus aculeatus* EG III (XG53, Cel12A) given as
weight % of degradation products.

| | Enzyme dosage (microgram/ml) | | | |
|---|---|---|---|---|
| | 0.1 | 0.1 | 10 | 10 |
| | Incubation time (hours) | | | |
| | 1 | 20 | 1 | 20 |
| $Cel_4$ | 0.17 | 0.91 | 1.19 | 0.00 |
| $Cel_5$ | 0.08 | 0.00 | 0.00 | 0.00 |
| $Cel_6$ | 0.00 | 0.00 | 0.00 | 0.00 |
| $Lam_2$ | 0.00 | 0.15 | 0.25 | 0.03 |
| $DP_3$ | 0.33 | 0.16 | 0.00 | 0.42 |
| $DP_4$ | 0.28 | 8.71 | 40.77 | 33.42 |
| $DP_5$ | 1.24 | 15.49 | 30.18 | 20.94 |
| $DP_6$ | 0.79 | 6.69 | 0.26 | 1.65 |
| DP >6 | 96.83 | 65.67 | 19.04 | 2.01 |

Glu: Glucose.
$Cel_i$: Cellooligo of DP i.
$Lam_2$: Laminaribiose.
$DP_i$: Oligosaccharide of DP i with a single beta-1,3 bond and the rest beta-1,4 bonds between the glucose units.
DP >6: Oligosaccharide consisting of more than 6 glucose units.

TABLE 14

Degradation products of barley beta-glucan with endoglucanase
*Aspergillus aculeatus* EG III (XG53, Cel12A) and
subsequent lichenase degradation given as weight %
of degradation products.

| | Enzyme dosage (microgram/ml) | | | |
|---|---|---|---|---|
| | 0.1 | 0.1 | 10 | 10 |
| | Incubation time (hours) | | | |
| | 1 | 20 | 1 | 20 |
| Glu | 1.08 | 6.84 | 7.12 | 16.22 |
| $Cel_2$ | 3.37 | 16.31 | 21.82 | 30.46 |
| $Cel_3$ | 3.90 | 5.25 | 4.40 | 7.66 |
| $Cel_4$ | 0.70 | 2.35 | 0.65 | 0.03 |
| $Cel_5$ | 0.58 | 0.00 | 0.00 | 0.10 |
| $Cel_6$ | 0.00 | 1.22 | 0.00 | 0.00 |
| $Lam_2$ | 4.12 | 16.93 | 16.24 | 5.07 |
| $DP_3$ | 57.22 | 33.12 | 6.11 | 0.99 |
| $DP_4$ | 18.69 | 12.16 | 38.91 | 35.81 |
| $DP_5$ | 4.39 | 1.46 | 2.41 | 2.62 |
| $DP_6$ | 3.44 | 2.16 | 0.26 | 0.78 |
| DP >6 | 2.51 | 2.19 | 2.08 | 0.26 |

Glu: Glucose.
$Cel_i$: Cellooligo of DP i.
$Lam_2$: Laminaribiose.
$DP_i$: Oligosaccharide of DP i with a single beta-1,3 bond and the rest beta-1,4 bonds between the glucose units.
DP >6: Oligosaccharide consisting of more than 6 glucose units.

EXAMPLE 4

Mashing and filtration performance

A conventional standard treatment of Ultraflo® 2.7 mg EP/kg dry matter (dm) grist (index 1,000) was compared to an experimental treatment with Ultraflo® 1.4 mg EP/kg dm grist supplemented with various endoglucanases. A dosage of 0.2 g Ultraflo®/kg DM grist equals 2.7 mg enzyme protein/kg dm grist.

TABLE 15

Effect of *Humicola insolens* EG I endoglucanase (Cel 7b, GH 7) and
*Humicola insolens* EG V endoglucanase, (Cel 45a, GH45).

| | Beta-glucan | Extract | Viscosity | Filterability | Best Performing |
|---|---|---|---|---|---|
| Ultraflo ® 2.7 mg EP/kg dm | 1.000 | 1.000 | 1.000 | 1.000 | — |
| Ultraflo ® 1.4 mg EP/kg dm + HI EG I 1.25 mg EP/kg dm | 1.184 | 0.997 | 1.032 | 0.904 | — |
| Ultraflo ® 1.4 mg EP/kg dm + HI EG V 1.25 mg EP/kg dm | 2.986 | 0.996 | 1.033 | 0.865 | — |
| Ultraflo ® 1.4 mg EP/kg dm + HI EG I 8 mg EP/kg dm | 0.377 | 0.992 | 1.021 | 0.962 | ** beta-glucan |
| Ultraflo ® 1.4 mg EP/kg dm + HI EG V 8 mg EP/kg dm | 3.262 | 1.000 | 1.055 | 0.865 | — |

Beta-glucan (n = 4),
Extract % (n = 4, based on dry matter),
Viscosity (n = 4, conv 8.6° Plato, cP),
Filterability (n = 2) after 10 min Ultraflo® 1.4 mg EP/kg dm supplemented with *H. insolens* EG I, Cel 7b (GH 7) 8 mg EP/kg dm reduced beta-glucan compared to the standard treatment (index 1.000).

TABLE 16

Effect of *Humicola insolens* EGIII endoglucanase, (Cel 12a, GH12) and *Humicola insolens* EG IV endoglucanase, (Cel 5a, GH12).

| | Beta-glucan | OD | Extract | Viscosity | Filterability | Best Performing |
|---|---|---|---|---|---|---|
| Ultraflo ® 2.7 mg EP/kg dm | 1.000 | 1.000 | 1.000 | 1.000 | 1.000 | — |
| Ultraflo ® 1.4 mg EP/kg dm + HI EG IV 1.25 mg EP/kg dm | 3.019 | 0.975 | 1.002 | 1.002 | 0.979 | — |
| Ultraflo ® 1.4 mg EP/kg dm + HI EG III 1.25 mg EP/kg dm | 0.628 | 0.949 | 1.000 | 0.999 | 0.957 | — |
| Ultraflo ® 1.4 mg EP/kg dm + HI EG IV 8.0 mg EP/kg dm | 2.045 | 1.013 | 0.999 | 1.006 | 1.085 | — |
| Ultraflo ® 1.4 mg EP/kg dm + HI EG III 8.0 mg EP/kg dm | 0.341 | 0.937 | 1.003 | 0.938 | 1.085 | *** beta-glucan, viscosity, filterability |

Beta-glucan (n = 4),
OD (n = 2),
Extract % (n = 4, based on dry matter),
Viscosity (n = 4, conv. 8.6° Plato, cP),
Filterability (n = 2) after 10 min The *H. insolens*, endoglucanase III, (Cel 12a, GH12) and Ultraflo® 1.4 mg EP/kg dm reduced the beta-glucan, O. D and viscosity while also improving filterability compared to the standard treatment.

TABLE 17

Effect of *Thermoascus aurantiacus* endoglucanase (GH 5).

| | Beta-glucan | OD | Extract | Viscosity | Filterability | Best Performing |
|---|---|---|---|---|---|---|
| Ultraflo ® 2.7 mg EP/kg dm | 1.000 | 1.000 | 1.000 | 1.000 | 1.000 | |
| Ultraflo ® 1.4 mg EP/kg dm + AT EG 5 1.25 mg EP/kg dm | 1.627 | 1.065 | 1.002 | 1.015 | 1.037 | |
| Ultraflo ® 1.4 mg EP/kg dm + AT EG 8 mg EP/kg dm | 0.432 | 1.033 | 1.001 | 1.017 | 1.000 | ** beta-glucan |

Beta-glucan (n = 4),
OD (n = 2),
Extract % (n = 4, based on dry matter),
Viscosity (n = 4, conv. 8.6° Plato, cP),
Filterability (n = 2) after 10 min Ultraflo® 1.4 mg EP/kg dm supplemented with the T. aurantiacus endoglucanase BG025 (GH 5) reduced the beta-glucan level significantly compared to the standard treatment.

A conventional standard treatment of Ultraflo® 0.2 g/kg DM grist (index 1,000) was compared to an experimental treatment with Ultraflo® 0.1 g/kg DM grist supplemented with various xylanases.

None of the two GH 11, type B xylanases from the fungi Bh and Cc had any positive effect on beta-glucan, OD, Extract recovery, viscosity or filterability.

TABLE 18

Effect of Bh xylanase B (GH 11, type B) & Cc xylanase II (GH 11 type B).

| | Beta-glucan | OD | Extract | Viscosity | Filterability | Best Performing |
|---|---|---|---|---|---|---|
| Ultraflo ® 2.7 mg EP/kg dm | 1.000 | 1.000 | 1.000 | 1.000 | 1.000 | — |
| Ultraflo ® 1.4 mg EP/kg dm + BH XYL 0.7 mg EP/kg dm | 3.223 | 1.100 | 1.000 | 1.032 | 1.082 | — |
| Ultraflo ® 1.4 mg EP/kg dm + CC XYL II 0.7 mg EP/kg dm | 3.279 | 1.025 | 0.998 | 1.028 | 1.012 | — |
| Ultraflo ® 1.4 mg EP/kg dm + BH XYL B 5 mg EP/kg dm | 3.231 | 1.025 | 1.000 | 1.048 | 1.035 | — |

TABLE 18-continued

Effect of Bh xylanase B (GH 11, type B) & Cc xylanase II (GH 11 type B).

|  | Beta-glucan | OD | Extract | Viscosity | Filterability | Best Performing |
|---|---|---|---|---|---|---|
| Ultraflo ® 1.4 mg EP/kg dm + CC XYL II 5 mg EP/kg dm | 3.213 | 1.038 | 1.003 | 1.030 | 1.082 | — |

Beta-glucan (n = 4),
OD (n = 2),
Extract % (n = 4, based on dry matter),
Viscosity (n = 4, conv. 8.6° Plato, cP),
Filterability (n = 2) after 10 min

TABLE 19

Effect of *Aspergillus aculeatus* xylanase I (GH10, type A) and *Myceliophotora thermophila* xylanase III (GH 11, type B).

|  | Beta-glucan | OD | Extract | Viscosity | Filterability | Best Performing |
|---|---|---|---|---|---|---|
| Ultraflo ® 2.7 mg EP/kg dm | 1.000 | 1.000 | 1.000 | 1.000 | 1.000 | — |
| Ultraflo ® 1.4 mg EP/kg dm + AA XYL I 5 mg EP/kg dm | 3.401 | 1.125 | 1.006 | 0.981 | 1.143 | *** Viscosity, filterability |
| Ultraflo ® 1.4 mg EP/kg dm + MT XYL II 5 mg EP/kg dm | 3.740 | 0.990 | 1.005 | 1.019 | 0.939 | — |
| Ultraflo ® 1.4 mg EP/kg dm + AA XYL I 0.7 mg EP/kg dm | 3.894 | 1.010 | 1.006 | 1.006 | 0.980 | — |
| Ultraflo ® 1.4 mg EP/kg dm + MT XYL II 0.7 mg EP/kg dm | 3.218 | 0.927 | 1.007 | 1.020 | 0.776 | — |

Beta-glucan (n = 4),
OD (n = 2),
Extract % (n = 4, based on dry matter),
Viscosity (n = 4, conv. 8.6° Plato, cP),
Filterability (n = 2) after 10 min

TABLE 20

Effect of *Thermomyces lanuginosus* xylanase (GH 11, type B) and *Aspergillus aculeatus* xylanase II (GH10, type A).

|  | Beta-glucan | Extract | Viscosity | Filterability | Best Performing |
|---|---|---|---|---|---|
| Ultraflo ® 2.7 mg EP/kg dm | 1.000 | 1.000 | 1.000 | 1.000 | — |
| Ultraflo ® 1.4 mg EP/kg dm + AA XYL II 0.7 mg EP/kg dm | 2.296 | 1.002 | 0.985 | 0.981 | — |
| Ultraflo ® 1.4 mg EP/kg dm + TL XYL 0.7 mg EP/kg dm | 2.375 | 0.994 | 1.015 | 0.868 | — |
| Ultraflo ® 1.4 mg EP/kg dm + AA XYL II 5 mg EP/kg dm | 2.152 | 1.000 | 0.970 | 1.075 | *** Viscosity, filterability |
| Ultraflo ® 1.4 mg EP/kg dm + TL XYL 5 mg EP/kg dm | 2.357 | 1.004 | 1.032 | 0.906 | — |

Beta-glucan (n = 4),
Extract % (n = 4, based on dry matter),
Viscosity (n = 4, conv 8.6° Plato, cP),
Filterability (n = 2) after 10 min The *Aspergillus aculeatus* xylanase I and *Aspergillus aculeatus* xylanase II reduced viscosity as well as improved filterability compared to the standard treatment.

A conventional standard treatment of Ultraflo® 0.2 g/kg dm grist (index 1.000) was compared to an experimental treatment with Viscozyme 0.1 g or 0 g/kg dm grist supplemented with *Aspergillus aculeatus* xylanase II and various endoglucanases.

TABLE 21

Effect of *Aspergillus aculeatus* betaglucanase EGII (XG 5) and *Aspergillus aculeatus* endoglucanase EGIII (XG53) in combination with *Aspergillus aculeatus* xylanase II and/or the Viscozyme® endoglucanase composition.

| | Beta-glucan | Extract | Viscosity | Filterability | Best Performing |
|---|---|---|---|---|---|
| Ultraflo ®: 2.7 mg EP/kg dm | 1.000 | 1.000 | 1.000 | 1.000 | |
| AA EG II 4 mg EP/kg dm<br>AA XYL II 4 mg EP/kg dm<br>Viscozyme ® 1.7 mg EP/kg dm | 5.795 | 0.997 | 0.981 | 1.140 | |
| AA EG III 1 mg EP/kg dm<br>AA XYL II 4 mg EP/kg dm<br>Viscozyme ® 1.7 mg EP/kg dm | 2.631 | 1.000 | 0.964 | 1.118 | **<br>viscosity,<br>filterability |
| AA EG III 2 mg EP/kg dm<br>AA XYL II 4 mg EP/kg dm<br>Viscozyme ® 1.7 mg EP/kg dm | 1.317 | 1.003 | 0.955 | 1.011 | |
| AA EG III 4 mg EP/kg dm,<br>AA XYL II 4 mg EP/kg dm | 0.918 | 1.004 | 0.956 | 1.236 | ***<br>beta-glucan,<br>viscosity,<br>filterability |
| AA EG II 8 mg EP/kg dm<br>AA XYL II 4 mg EP/kg dm | 6.601 | 1.003 | 0.977 | 1.096 | |

Beta-glucan (n = 4),
Extract % (n = 4, based on dry matter),
Viscosity (n = 4, conv. 8.6° Plato, cP),
Filterability (n = 2) after 10 min A combination of *Aspergillus aculeatus* Xylanase II and *Aspergillus aculeatus* endoglucanase EG III had a significant effect on beta-glucan, viscosity and filterability.

TABLE 22

Comparison of increasing amounts of Viscozyme® and of a composition of the present invention. Absolute values.

| | Beta-glucan | OD | Extract % | Viscosity |
|---|---|---|---|---|
| Viscozyme ® 3.6 mg EP/kg dm | 189 | 0.030 | 85.0 | 1.38 |
| Viscozyme ® 9 mg EP/kg dm | 155 | 0.030 | 85.0 | 1.35 |
| Viscozyme ® 13.5 mg EP/kg dm | 127 | 0.031 | 85.2 | 1.34 |
| Viscozyme ® 18 mg EP/kg dm | 101 | 0.028 | 85.5 | 1.32 |
| Viscozyme ® 27 mg EP/kg dm | 75 | 0.030 | 85.7 | 1.30 |
| Viscozyme ® 3.6 mg EP/kg dm<br>AA EG III 2 mg EP/kg dm<br>AA XYL II 4 mg EP/kg dm | 0 | 0.030 | 85.8 | 1.22 |

Beta-glucan (mg/l, n = 4),
OD (n = 2),
Extract % (n = 4, extract in dry malt, % (m/m)),
Viscosity (n = 4, conv. 8.6° Plato, cP), A composition comprising Viscozyme® 3.6 mg EP/kg dm, *Aspergillus aculeatus* EG III 2 mg EP/kg dm, and *Aspergillus aculeatus* Xylanase II 4 mg EP/kg dm had a significantly more positive effect on beta-glucan, OD, extract recovery, and viscosity than had a dosage of 7.5 times the conventional standard dosage of Viscozyme® (Std. dosage=3.6 mg EP/kg dm) (Table 22).

EXAMPLE 5

Quantification of Protein Bands in SDS-PAGE Gels

The enzyme composition was diluted 250 times in deionized water and loaded onto a 4-20% Tris-glycine SDS-PAGE gel (Nu Page, Invitrogen) and the electrophoresis was conducted as described by the manufacturer.

After electrophoresis the gel was stained with GelCode Blue (Pierce) o/n and subsequently decolorized in water to the background became clear.

The resulting gel was then scanned using a densitometer and analyzed by the ImageMaster™ v. 1 0 software from Amersham Biosciences following the protocol from the manufacturer. The results are expressed as % band density of total density in a given lane.

The total amount of protein in the enzyme samples were measured using the Micro BCA kit from Pierce using the protocol supplied with the kit.

The invention claimed is:

1. A process for production of a mash having enhanced filterability or improved extract yield after filtration, or enhanced filterability and improved extract yield after filtration, which comprises preparing a mash in the presence of enzyme activities and filtering the mash to obtain a wort, wherein the enzyme activities comprise
a xylanase of GH family 10 having at least 90% homology to SEQ ID NO: 9 present in an amount of at least 15% w/w of the total xylanase and endoglucanase enzyme protein, and
an endoglucanase having at least 90% homology to SEQ ID NO:7.

2. The process of claim 1, wherein the xylanase is present in an amount of at least 20% w/w of the total xylanase and endoglucanase enzyme protein.

3. The process of claim 1, wherein the xylanase is present in an amount of at least 70% w/w of the total xylanase and endoglucanase enzyme protein.

4. The process of claim 1, wherein the endoglucanase is present in an amount of at least 40% w/w of the total xylanase and endoglucanase enzyme protein.

5. The process of claim 1, wherein the endoglucanase is present in an amount of at least 45% w/w of the total xylanase and endoglucanase enzyme protein.

6. The process of claim 1, wherein the endoglucanase is present in an amount of at least 80% w/w of the total xylanase and endoglucanase enzyme protein.

7. The process of claim 1, wherein the xylanase is obtained from a bacterium.

8. The process of claim 1, wherein the xylanase is obtained from a strain of *Aspergillus*.

9. The process of claim 1, wherein the xylanase comprises the amino acid sequence of SEQ ID NO: 9.

10. The process of claim 1, wherein the xylanase consists of the amino acid sequence of SEQ ID NO: 9.

11. The process of claim 1, wherein the endoglucanase is obtained from a bacterium.

12. The process of claim 1, wherein the endoglucanase is obtained from a strain of *Thermoascus*.

13. The process of claim 1, wherein the endoglucanase comprises the amino acid sequence of SEQ ID NO: 7.

14. The process of claim 1, wherein the endoglucanase consists of the amino acid sequence of SEQ ID NO: 7.

15. The process of claim 1, wherein at least one additional enzyme is present, which enzyme is selected from the group consisting of arabinofuranosidase, ferulic acid esterase and xylan acetyl esterase.

* * * * *

```
                        SEQUENCE LISTING

<160> NUMBER OF SEQ ID NOS: 20

<210> SEQ ID NO 1
<211> LENGTH: 332
<212> TYPE: PRT
<213> ORGANISM: Aspergillus aculeatus

<400> SEQUENCE: 1

Met Lys Leu Leu Asn Leu Leu Val Ala Ala Ala Ala Ala Gly Ser Ala
1               5                   10                  15
```

```
Val Ala Ala Pro Thr His Glu His Thr Lys Arg Ala Ser Val Phe Glu
             20                  25                  30

Trp Ile Gly Ser Asn Glu Ser Asp Ala Glu Phe Gly Thr Ala Ile Pro
         35                  40                  45

Gly Thr Trp Gly Ile Asp Tyr Ile Phe Pro Asp Thr Ser Ala Ile Ala
 50                  55                  60

Thr Leu Val Ser Lys Gly Met Asn Ile Phe Arg Val Gln Phe Met Met
65                  70                  75                  80

Glu Arg Leu Val Pro Asn Ser Met Thr Gly Ser Tyr Asp Asp Ala Tyr
                 85                  90                  95

Leu Asn Asn Leu Thr Thr Val Val Asn Ala Ile Ala Ala Ala Gly Val
             100                 105                 110

His Ala Ile Val Asp Pro His Asn Tyr Gly Arg Tyr Asn Asn Glu Ile
         115                 120                 125

Ile Ser Ser Thr Ala Asp Phe Gln Thr Phe Trp Gln Asn Leu Ala Gly
130                 135                 140

Gln Phe Lys Asp Asn Asp Leu Val Ile Phe Asp Thr Asn Asn Glu Tyr
145                 150                 155                 160

Asn Thr Met Asp Gln Thr Leu Val Leu Asp Leu Asn Gln Ala Ala Ile
                 165                 170                 175

Asp Gly Ile Arg Ala Ala Gly Ala Thr Ser Gln Tyr Ile Phe Ala Glu
             180                 185                 190

Gly Asn Ser Trp Ser Gly Ala Trp Thr Trp Ala Asp Ile Asn Asp Asn
         195                 200                 205

Met Lys Ala Leu Thr Asp Pro Gln Asp Lys Leu Val Tyr Glu Met His
210                 215                 220

Gln Tyr Leu Asp Ser Asp Gly Ser Gly Thr Ser Gly Val Cys Val Ser
225                 230                 235                 240

Glu Thr Ile Gly Ala Glu Arg Leu Gln Ala Ala Thr Gln Trp Leu Lys
                 245                 250                 255

Asp Asn Gly Lys Val Asp Ile Leu Gly Glu Tyr Ala Gly Gly Ala Asn
             260                 265                 270

Asp Val Cys Arg Thr Ala Ile Ala Gly Met Leu Glu Tyr Met Ala Asn
         275                 280                 285

Asn Thr Asp Val Trp Lys Gly Ala Val Trp Trp Thr Ala Gly Pro Trp
290                 295                 300

Trp Ala Asp Tyr Met Phe Ser Met Glu Pro Pro Ser Gly Pro Ala Tyr
305                 310                 315                 320

Ser Gly Met Leu Asp Val Leu Glu Pro Tyr Leu Gly
                 325                 330

<210> SEQ ID NO 2
<211> LENGTH: 238
<212> TYPE: PRT
<213> ORGANISM: Aspergillus aculeatus

<400> SEQUENCE: 2

Met Lys Leu Ser Leu Leu Ser Leu Ala Thr Leu Ala Ser Ala Ala Ser
1               5                   10                  15

Leu Gln Arg Arg Ser Asp Phe Cys Gly Gln Trp Asp Thr Ala Thr Ala
             20                  25                  30

Gly Asp Phe Thr Leu Tyr Asn Asp Leu Trp Gly Glu Ser Ala Gly Thr
         35                  40                  45

Gly Ser Gln Cys Thr Gly Val Asp Ser Tyr Ser Gly Asp Thr Ile Ala
 50                  55                  60
```

```
Trp His Thr Ser Trp Ser Trp Ser Gly Gly Ser Ser Val Lys Ser
 65                  70                  75                  80

Tyr Val Asn Ala Ala Leu Thr Phe Thr Pro Thr Gln Leu Asn Cys Ile
                 85                  90                  95

Ser Ser Ile Pro Thr Thr Trp Lys Trp Ser Tyr Ser Gly Ser Ser Ile
            100                 105                 110

Val Ala Asp Val Ala Tyr Asp Thr Phe Leu Ala Glu Thr Ala Ser Gly
            115                 120                 125

Ser Ser Lys Tyr Glu Ile Met Val Trp Leu Ala Ala Leu Gly Gly Ala
130                 135                 140

Gly Pro Ile Ser Ser Thr Gly Ser Thr Ile Ala Thr Pro Thr Ile Ala
145                 150                 155                 160

Gly Val Asn Trp Lys Leu Tyr Ser Gly Pro Asn Gly Asp Thr Val
                165                 170                 175

Tyr Ser Phe Val Ala Asp Ser Thr Thr Glu Ser Phe Ser Gly Asp Leu
            180                 185                 190

Asn Asp Phe Phe Thr Tyr Leu Val Asp Asn Glu Gly Val Ser Asp Glu
            195                 200                 205

Leu Tyr Leu Thr Thr Leu Glu Ala Gly Thr Glu Pro Phe Thr Gly Ser
    210                 215                 220

Asn Ala Lys Leu Thr Val Ser Glu Tyr Ser Ile Ser Ile Glu
225                 230                 235

<210> SEQ ID NO 3
<211> LENGTH: 435
<212> TYPE: PRT
<213> ORGANISM: Humicola insolens

<400> SEQUENCE: 3

Met Ala Arg Gly Thr Ala Leu Leu Gly Leu Thr Ala Leu Leu Leu Gly
  1               5                  10                  15

Leu Val Asn Gly Gln Lys Pro Gly Glu Thr Lys Glu Val His Pro Gln
                 20                  25                  30

Leu Thr Thr Phe Arg Cys Thr Lys Arg Gly Gly Cys Lys Pro Ala Thr
             35                  40                  45

Asn Phe Ile Val Leu Asp Ser Leu Ser His Pro Ile His Arg Ala Glu
 50                  55                  60

Gly Leu Gly Pro Gly Gly Cys Gly Asp Trp Gly Asn Pro Pro Pro Lys
 65                  70                  75                  80

Asp Val Cys Pro Asp Val Glu Ser Cys Ala Lys Asn Cys Ile Met Glu
                 85                  90                  95

Gly Ile Pro Asp Tyr Ser Gln Tyr Gly Val Thr Thr Asn Gly Thr Ser
            100                 105                 110

Leu Arg Leu Gln His Ile Leu Pro Asp Gly Arg Val Pro Ser Pro Arg
            115                 120                 125

Val Tyr Leu Leu Asp Lys Thr Lys Arg Arg Tyr Glu Met Leu His Leu
            130                 135                 140

Thr Gly Phe Glu Phe Thr Phe Asp Val Asp Ala Thr Lys Leu Pro Cys
145                 150                 155                 160

Gly Met Asn Ser Ala Leu Tyr Leu Ser Glu Met His Pro Thr Gly Ala
                165                 170                 175

Lys Ser Lys Tyr Asn Pro Gly Gly Ala Tyr Tyr Gly Thr Gly Tyr Cys
            180                 185                 190

Asp Ala Gln Cys Phe Val Thr Pro Phe Ile Asn Gly Leu Gly Asn Ile
```

```
                195                 200                 205
Glu Gly Lys Gly Ser Cys Cys Asn Glu Met Asp Ile Trp Glu Ala Asn
    210                 215                 220
Ser Arg Ala Ser His Val Ala Pro His Thr Cys Asn Lys Lys Gly Leu
225                 230                 235                 240
Tyr Leu Cys Glu Gly Glu Cys Ala Phe Glu Gly Val Cys Asp Lys
                245                 250                 255
Asn Gly Cys Gly Trp Asn Asn Tyr Arg Val Asn Val Thr Asp Tyr Tyr
            260                 265                 270
Gly Arg Gly Glu Glu Phe Lys Val Asn Thr Leu Lys Pro Phe Thr Val
                275                 280                 285
Val Thr Gln Phe Leu Ala Asn Arg Arg Gly Lys Leu Glu Lys Ile His
            290                 295                 300
Arg Phe Tyr Val Gln Asp Gly Lys Val Ile Glu Ser Phe Tyr Thr Asn
305                 310                 315                 320
Lys Glu Gly Val Pro Tyr Thr Asn Met Ile Asp Asp Glu Phe Cys Glu
                325                 330                 335
Ala Thr Gly Ser Arg Lys Tyr Met Glu Leu Gly Ala Thr Gln Gly Met
            340                 345                 350
Gly Glu Ala Leu Thr Arg Gly Met Val Leu Ala Met Ser Ile Trp Trp
                355                 360                 365
Asp Gln Gly Gly Asn Met Glu Trp Leu Asp His Gly Glu Ala Gly Pro
            370                 375                 380
Cys Ala Lys Gly Glu Gly Ala Pro Ser Asn Ile Val Gln Val Glu Pro
385                 390                 395                 400
Phe Pro Glu Val Thr Tyr Thr Asn Leu Arg Trp Gly Glu Ile Gly Ser
                405                 410                 415
Thr Tyr Gln Glu Val Gln Lys Pro Lys Pro Lys Pro Gly His Gly Pro
            420                 425                 430
Arg Ser Asp
        435

<210> SEQ ID NO 4
<211> LENGTH: 254
<212> TYPE: PRT
<213> ORGANISM: Humicola insolens

<400> SEQUENCE: 4

Met Leu Lys Ser Ala Leu Leu Leu Gly Pro Ala Ala Val Ser Val Gln
1               5                   10                  15
Ser Ala Ser Ile Pro Thr Ile Pro Ala Asn Leu Glu Pro Arg Gln Ile
                20                  25                  30
Arg Ser Leu Cys Glu Leu Tyr Gly Tyr Trp Ser Gly Asn Gly Tyr Glu
            35                  40                  45
Leu Leu Asn Asn Leu Trp Gly Lys Asp Thr Ala Thr Ser Gly Trp Gln
        50                  55                  60
Cys Thr Tyr Leu Asp Gly Thr Asn Asn Gly Ile Gln Trp Ser Thr
65                  70                  75                  80
Ala Trp Glu Trp Gln Gly Ala Pro Asp Asn Val Lys Ser Tyr Pro Tyr
                85                  90                  95
Val Gly Lys Gln Ile Gln Arg Gly Arg Lys Ile Ser Asp Ile Asn Ser
            100                 105                 110
Met Arg Thr Ser Val Ser Trp Thr Tyr Asp Arg Thr Asp Ile Arg Ala
        115                 120                 125
```

```
Asn Val Ala Tyr Asp Val Phe Thr Ala Arg Asp Pro Asp His Pro Asn
    130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175

Thr Trp Asp Leu Trp Thr Gly Tyr Asn Gly Asn Met Arg Val Tyr Ser
            180                 185                 190

Phe Leu Pro Pro Ser Gly Asp Ile Arg Asp Phe Ser Cys Asp Ile Lys
        195                 200                 205

Asp Phe Phe Asn Tyr Leu Glu Arg Asn His Gly Tyr Pro Ala Arg Glu
210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
                245                 250

<210> SEQ ID NO 5
<211> LENGTH: 388
<212> TYPE: PRT
<213> ORGANISM: Humicola insolens

<400> SEQUENCE: 5

Met Lys His Ser Val Leu Ala Gly Leu Phe Ala Thr Gly Ala Leu Ala
1               5                   10                  15

Gln Gly Gly Ala Trp Gln Gln Cys Gly Gly Val Gly Phe Ser Gly Ser
                20                  25                  30

Thr Ser Cys Val Ser Gly Tyr Thr Cys Val Tyr Leu Asn Asp Trp Tyr
            35                  40                  45

Ser Gln Cys Gln Pro Gln Pro Thr Thr Leu Arg Thr Thr Thr Thr Pro
        50                  55                  60

Gly Ala Thr Ser Thr Thr Arg Ser Ala Pro Ala Ala Thr Ser Thr Thr
65                  70                  75                  80

Pro Ala Lys Gly Lys Phe Lys Trp Phe Gly Ile Asn Gln Ser Cys Ala
                85                  90                  95

Glu Phe Gly Lys Gly Glu Tyr Pro Gly Leu Trp Gly Lys His Phe Thr
                100                 105                 110

Phe Pro Ser Thr Ser Ser Ile Gln Thr His Ile Asn Asp Gly Phe Asn
            115                 120                 125

Met Phe Arg Val Ala Phe Ser Met Glu Arg Leu Ala Pro Asn Gln Leu
        130                 135                 140

Asn Ala Ala Phe Asp Ala Asn Tyr Leu Arg Asn Leu Thr Glu Thr Val
145                 150                 155                 160

Asn Phe Ile Thr Gly Lys Gly Lys Tyr Ala Met Leu Asp Pro His Asn
                165                 170                 175

Phe Gly Arg Tyr Tyr Glu Arg Ile Ile Thr Asp Lys Ala Ala Phe Ala
            180                 185                 190

Ser Phe Phe Thr Lys Leu Ala Thr His Phe Ala Ser Asn Pro Leu Val
        195                 200                 205

Val Phe Asp Thr Asn Asn Glu Tyr His Asp Met Asp Gln Gln Leu Val
210                 215                 220

Phe Asp Leu Asn Gln Ala Ala Ile Asp Ala Ile Arg Ala Ala Gly Ala
225                 230                 235                 240

Thr Ser Gln Tyr Ile Met Val Glu Gly Asn Ser Trp Thr Gly Ala Trp
                245                 250                 255
```

Thr Trp Asn Val Thr Asn Asn Leu Ala Ala Leu Arg Asp Pro Glu
        260                 265                 270

Asn Lys Leu Val Tyr Gln Met His Gln Tyr Leu Asp Ser Asp Gly Ser
            275                 280                 285

Gly Thr Ser Thr Ala Cys Val Ser Thr Gln Val Gly Leu Gln Arg Val
        290                 295                 300

Ile Gly Ala Thr Asn Trp Leu Arg Gln Asn Gly Lys Val Gly Leu Leu
305                 310                 315                 320

Gly Glu Phe Ala Gly Gly Ala Asn Ser Val Cys Gln Gln Ala Ile Glu
                325                 330                 335

Gly Met Leu Thr His Leu Gln Glu Asn Ser Asp Val Trp Thr Gly Ala
            340                 345                 350

Leu Trp Trp Ala Gly Gly Pro Trp Gly Asp Tyr Ile Tyr Ser Phe
        355                 360                 365

Glu Pro Pro Ser Gly Ile Gly Tyr Thr Tyr Tyr Asn Ser Leu Leu Lys
        370                 375                 380

Lys Tyr Val Pro
385

<210> SEQ ID NO 6
<211> LENGTH: 305
<212> TYPE: PRT
<213> ORGANISM: Humicola insolens

<400> SEQUENCE: 6

Met Arg Ser Ser Pro Leu Leu Arg Ser Ala Val Ala Ala Leu Pro
1               5                   10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Ser Thr Ser Ser

```
            225                 230                 235                 240
Pro Val Asn Gln Pro Thr Ser Thr Ser Thr Thr Ser Thr Ser Thr Thr
                245                 250                 255

Ser Ser Pro Pro Val Gln Pro Thr Thr Pro Ser Gly Cys Thr Ala Glu
                260                 265                 270

Arg Trp Ala Gln Cys Gly Gly Asn Gly Trp Ser Gly Cys Thr Thr Cys
                275                 280                 285

Val Ala Gly Ser Thr Cys Thr Lys Ile Asn Asp Trp Tyr His Gln Cys
                290                 295                 300

Leu
305

<210> SEQ ID NO 7
<211> LENGTH: 335
<212> TYPE: PRT
<213> ORGANISM: Thermoascus aurantiacus

<400> SEQUENCE: 7

Met Lys Leu Gly Ser Leu Val Leu Ala Leu Ser Ala Ala Arg Leu Thr
1               5                   10                  15

Leu Ser Ala Pro Leu Ala Asp Arg Lys Gln Glu Thr Lys Arg Ala Lys
                20                  25                  30

Val Phe Gln Trp Phe Gly Ser Asn Glu Ser Gly Ala Glu Phe Gly Ser
                35                  40                  45

Gln Asn Leu Pro Gly Val Glu Gly Lys Asp Tyr Ile Trp Pro Asp Pro
            50                  55                  60

Asn Thr Ile Asp Thr Leu Ile Ser Lys Gly Met Asn Ile Phe Arg Val
65                  70                  75                  80

Pro Phe Met Met Glu Arg Leu Val Pro Asn Ser Met Thr Gly Ser Pro
                85                  90                  95

Asp Pro Asn Tyr Leu Ala Asp Leu Ile Ala Thr Val Asn Ala Ile Thr
                100                 105                 110

Gln Lys Gly Ala Tyr Ala Val Val Asp Pro His Asn Tyr Gly Arg Tyr
                115                 120                 125

Tyr Asn Ser Ile Ile Ser Ser Pro Ser Asp Phe Gln Thr Phe Trp Lys
            130                 135                 140

Thr Val Ala Ser Gln Phe Ala Ser Asn Pro Leu Val Ile Phe Asp Thr
145                 150                 155                 160

Asn Asn Glu Tyr His Asp Met Asp Gln Thr Leu Val Leu Asn Leu Asn
                165                 170                 175

Gln Ala Ala Ile Asp Gly Ile Arg Ser Ala Gly Ala Thr Ser Gln Tyr
                180                 185                 190

Ile Phe Val Glu Gly Asn Ser Trp Thr Gly Ala Trp Thr Trp Thr Asn
                195                 200                 205

Val Asn Asp Asn Met Lys Ser Leu Thr Asp Pro Ser Asp Lys Ile Ile
            210                 215                 220

Tyr Glu Met His Gln Tyr Leu Asp Ser Asp Gly Ser Gly Thr Ser Ala
225                 230                 235                 240

Thr Cys Val Ser Ser Thr Ile Gly Gln Glu Arg Ile Thr Ser Ala Thr
                245                 250                 255

Gln Trp Leu Arg Ala Asn Gly Lys Lys Gly Ile Ile Gly Glu Phe Ala
                260                 265                 270

Gly Gly Ala Asn Asp Val Cys Glu Thr Ala Ile Thr Gly Met Leu Asp
                275                 280                 285
```

```
Tyr Met Ala Gln Asn Thr Asp Val Trp Thr Gly Ala Ile Trp Trp Ala
    290                 295                 300
Ala Gly Pro Trp Trp Gly Asp Tyr Ile Phe Ser Met Glu Pro Asp Asn
305                 310                 315                 320
Gly Ile Ala Tyr Gln Gln Ile Leu Pro Ile Leu Thr Pro Tyr Leu
                325                 330                 335

<210> SEQ ID NO 8
<211> LENGTH: 327
<212> TYPE: PRT
<213> ORGANISM: Aspergillus aculeatus

<400> SEQUENCE: 8

Met Val Gln Ile Lys Ala Ala Leu Ala Val Leu Phe Ala Ser Asn
1               5                   10                  15
Val Leu Ser Asn Pro Ile Glu Pro Arg Gln Ala Ser Val Ser Ile Asp
                20                  25                  30
Ala Lys Phe Lys Ala His Gly Lys Lys Tyr Leu Gly Thr Ile Gly Asp
            35                  40                  45
Gln Tyr Thr Leu Asn Lys Asn Ala Lys Thr Pro Ala Ile Ile Lys Ala
50                  55                  60
Asp Phe Gly Gln Leu Thr Pro Glu Asn Ser Met Lys Trp Asp Ala Thr
65                  70                  75                  80
Glu Pro Asn Arg Gly Gln Phe Ser Phe Ser Gly Ser Asp Tyr Leu Val
                85                  90                  95
Asn Phe Ala Gln Ser Asn Gly Lys Leu Ile Arg Gly His Thr Leu Val
            100                 105                 110
Trp His Ser Gln Leu Pro Ser Trp Val Gln Ser Ile Ser Asp Lys Asn
        115                 120                 125
Thr Leu Ile Gln Val Met Gln Asn His Ile Thr Thr Val Met Gln Arg
130                 135                 140
Tyr Lys Gly Lys Val Tyr Ala Trp Asp Val Val Asn Glu Ile Phe Asn
145                 150                 155                 160
Glu Asp Gly Ser Leu Cys Gln Ser His Phe Tyr Asn Val Ile Gly Glu
                165                 170                 175
Asp Tyr Val Arg Ile Ala Phe Glu Thr Ala Arg Ala Val Asp Pro Asn
            180                 185                 190
Ala Lys Leu Tyr Ile Asn Asp Tyr Asn Leu Asp Ser Ala Ser Tyr Pro
        195                 200                 205
Lys Leu Thr Gly Leu Val Asn His Val Lys Lys Trp Val Ala Ala Gly
210                 215                 220
Val Pro Ile Asp Gly Ile Gly Ser Gln Thr His Leu Ser Ala Gly Ala
225                 230                 235                 240
Gly Ala Ala Val Ser Gly Ala Leu Asn Ala Leu Ala Gly Ala Gly Thr
                245                 250                 255
Lys Glu Val Ala Ile Thr Glu Leu Asp Ile Ala Gly Ala Ser Ser Thr
            260                 265                 270
Asp Tyr Val Asn Val Val Lys Ala Cys Leu Asn Gln Pro Lys Cys Val
        275                 280                 285
Gly Ile Thr Val Trp Gly Ser Ser Asp Pro Asp Ser Trp Arg Ser Ser
290                 295                 300
Ser Ser Pro Leu Leu Phe Asp Ser Asn Tyr Asn Pro Lys Ala Ala Tyr
305                 310                 315                 320
Thr Ala Ile Ala Asn Ala Leu
                325
```

<210> SEQ ID NO 9
<211> LENGTH: 406
<212> TYPE: PRT
<213> ORGANISM: Aspergillus aculeatus

<400> SEQUENCE: 9

Met Val Gly Leu Leu Ser Ile Thr Ala Ala Leu Ala Ala Thr Val Leu
1               5                   10                  15

Pro Asn Ile Val Ser Ala Val Gly Leu Asp Gln Ala Ala Val Ala Lys
            20                  25                  30

Gly Leu Gln Tyr Phe Gly Thr Ala Thr Asp Asn Pro Glu Leu Thr Asp
        35                  40                  45

Ile Pro Tyr Val Thr Gln Leu Asn Asn Thr Ala Asp Phe Gly Gln Ile
    50                  55                  60

Thr Pro Gly Asn Ser Met Lys Trp Asp Ala Thr Glu Pro Ser Gln Gly
65                  70                  75                  80

Thr Phe Thr Phe Thr Lys Gly Asp Val Ile Ala Asp Leu Ala Glu Gly
                85                  90                  95

Asn Gly Gln Tyr Leu Arg Cys His Thr Leu Val Trp Tyr Asn Gln Leu
            100                 105                 110

Pro Ser Trp Val Thr Ser Gly Thr Trp Thr Asn Ala Thr Leu Thr Ala
        115                 120                 125

Ala Leu Lys Asn His Ile Thr Asn Val Val Ser His Tyr Lys Gly Lys
    130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Asp Pro Asp Ala Lys Leu Phe
            180                 185                 190

Tyr Asn Asp Tyr Asn Leu Glu Tyr Gly Gly Ala Lys Ala Ala Ser Ala
        195                 200                 205

Arg Ala Ile Val Gln Leu Val Lys Asn Ala Gly Ala Lys Ile Asp Gly
    210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Leu Pro Thr Thr Ala Thr
            260                 265                 270

Thr Leu Ala Gln Gln Ser Ser Asp Phe Gln Ala Leu Val Gln Ser Cys
        275                 280                 285

Val Gln Thr Thr Gly Cys Val Gly Phe Thr Ile Trp Asp Trp Thr Asp
    290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Thr Ala
            340                 345                 350

Thr Ala Thr Gly Lys Thr Thr Thr Thr Thr Gly Ala Thr Ser Thr
        355                 360                 365

Gly Thr Thr Ala Ala His Trp Gly Gln Cys Gly Gly Leu Asn Trp Ser

```
                    370                 375                 380
Gly Pro Thr Ala Cys Ala Thr Gly Tyr Thr Cys Thr Tyr Val Asn Asp
385                 390                 395                 400

Tyr Tyr Ser Gln Cys Leu
                405

<210> SEQ ID NO 10
<211> LENGTH: 231
<212> TYPE: PRT
<213> ORGANISM: Aspergillus aculeatus

<400> SEQUENCE: 10

Met Ala Arg Leu Ser Gln Phe Leu Leu Ala Cys Ala Leu Ala Val Lys
1               5                   10                  15

Ala Phe Ala Ala Pro Ala Ala Glu Pro Val Glu Glu Arg Gly Pro Asn
                20                  25                  30

Phe Phe Ser Ala Leu Ala Gly Arg Ser Thr Gly Ser Ser Thr Gly Tyr
            35                  40                  45

Ser Asn Gly Tyr Tyr Ser Phe Trp Thr Asp Gly Ala Ser Gly Asp
50                  55                  60

Val Glu Tyr Ser Asn Gly Ala Gly Gly Ser Tyr Ser Val Thr Trp Ser
65                  70                  75                  80

Ser Ala Ser Asn Phe Val Gly Gly Lys Gly Trp Asn Pro Gly Ser Ala
                85                  90                  95

His Asp Ile Thr Tyr Ser Gly Ser Trp Thr Ser Thr Gly Asn Ser Asn
            100                 105                 110

Ser Tyr Leu Ser Val Tyr Gly Trp Thr Thr Gly Pro Leu Val Glu Tyr
        115                 120                 125

Tyr Ile Leu Glu Asp Tyr Gly Glu Tyr Asn Pro Gly Ser Ala Gly Thr
    130                 135                 140

Tyr Lys Gly Ser Val Tyr Ser Asp Gly Ser Tyr Asn Ile Tyr Thr
145                 150                 155                 160

Ala Thr Arg Thr Asn Ala Pro Ser Ile Gln Gly Thr Ala Thr Phe Thr
                165                 170                 175

Gln Tyr Trp Ser Ile Arg Gln Thr Lys Arg Val Gly Gly Thr Val Thr
            180                 185                 190

Thr Ala Asn His Phe Asn Ala Trp Ala Lys Leu Gly Met Asn Leu Gly
        195                 200                 205

Thr His Asn Tyr Gln Ile Val Ala Thr Glu Gly Tyr Tyr Ser Ser Gly
    210                 215                 220

Ser Ala Ser Ile Thr Val Ala
225                 230

<210> SEQ ID NO 11
<211> LENGTH: 227
<212> TYPE: PRT
<213> ORGANISM: Humicola insolens

<400> SEQUENCE: 11

Met Val Ser Leu Lys Ser Val Leu Ala Ala Thr Ala Val Ser Ser
1               5                   10                  15

Ala Ile Ala Ala Pro Phe Asp Phe Val Pro Arg Asp Asn Ser Thr Ala
                20                  25                  30

Leu Gln Ala Arg Gln Val Thr Pro Asn Ala Glu Gly Trp His Asn Gly
            35                  40                  45

Tyr Phe Tyr Ser Trp Trp Ser Asp Gly Gly Gly Gln Val Gln Tyr Thr
```

```
                    50                  55                  60
Asn Leu Glu Gly Ser Arg Tyr Gln Val Arg Trp Arg Asn Thr Gly Asn
 65                  70                  75                  80

Phe Val Gly Gly Lys Gly Trp Asn Pro Gly Thr Gly Arg Thr Ile Asn
                     85                  90                  95

Tyr Gly Gly Tyr Phe Asn Pro Gln Gly Asn Gly Tyr Leu Ala Val Tyr
                    100                 105                 110

Gly Trp Thr Arg Asn Pro Leu Val Glu Tyr Tyr Val Ile Glu Ser Tyr
                115                 120                 125

Gly Thr Tyr Asn Pro Gly Ser Gln Ala Gln Tyr Lys Gly Thr Phe Tyr
                130                 135                 140

Thr Asp Gly Asp Gln Tyr Asp Ile Phe Val Ser Thr Arg Tyr Asn Gln
145                 150                 155                 160

Pro Ser Ile Asp Gly Thr Arg Thr Phe Gln Gln Tyr Trp Ser Ile Arg
                165                 170                 175

Lys Asn Lys Arg Val Gly Gly Ser Val Asn Met Gln Asn His Phe Asn
                180                 185                 190

Ala Trp Gln Gln His Gly Met Pro Leu Gly Gln His Tyr Tyr Gln Val
                195                 200                 205

Val Ala Thr Glu Gly Tyr Gln Ser Ser Gly Glu Ser Asp Ile Tyr Val
                210                 215                 220

Gln Thr His
225

<210> SEQ ID NO 12
<211> LENGTH: 389
<212> TYPE: PRT
<213> ORGANISM: Humicola insolens

<400> SEQUENCE: 12

Met Arg Ser Ile Ala Leu Ala Leu Ala Ala Ala Pro Ala Val Leu Ala
 1               5                  10                  15

Gln Ser Gln Leu Trp Gly Gln Cys Gly Gly Ile Gly Trp Asn Gly Pro
                20                  25                  30

Thr Thr Cys Val Ser Gly Ala Thr Cys Thr Lys Ile Asn Asp Trp Tyr
                35                  40                  45

His Gln Cys Leu Pro Gly Gly Asn Asn Asn Pro Pro Pro Ala Thr
 50                  55                  60

Thr Ser Gln Trp Thr Pro Pro Ala Gln Thr Ser Ser Asn Pro Pro
 65                  70                  75                  80

Pro Thr Gly Gly Gly Gly Asn Thr Leu His Glu Lys Phe Lys Ala
                 85                  90                  95

Arg Gly Lys Gln Tyr Phe Gly Thr Glu Ile Asp His Tyr His Leu Asn
                100                 105                 110

Asn Asn Gln Leu Met Glu Ile Ala Arg Arg Glu Phe Gly Gln Ile Thr
                115                 120                 125

His Glu Asn Ser Met Lys Trp Asp Ala Thr Glu Pro Ser Arg Gly Ser
                130                 135                 140

Phe Ser Phe Gly Asn Ala Asp Arg Val Val Asp Trp Ala Thr Ser Asn
145                 150                 155                 160

Gly Lys Leu Ile Arg Gly His Thr Leu Leu Trp His Ser Gln Leu Pro
                165                 170                 175

Gln Trp Val Gln Asn Ile Asn Asp Arg Asn Thr Leu Thr Gln Val Ile
                180                 185                 190
```

```
Glu Asn His Val Arg Thr Val Met Thr Arg Tyr Lys Gly Lys Ile Phe
            195                 200                 205

His Tyr Asp Val Val Asn Glu Ile Leu Asp Glu Asn Gly Gly Leu Arg
        210                 215                 220

Asn Ser Val Phe Ser Arg Val Leu Gly Glu Asp Phe Val Gly Ile Ala
225                 230                 235                 240

Phe Arg Ala Ala Arg Ala Ala Asp Pro Asp Ala Lys Leu Tyr Ile Asn
                245                 250                 255

Asp Tyr Asn Leu Asp Ser Ala Asn Tyr Ala Lys Thr Arg Gly Met Ile
            260                 265                 270

Asn Leu Val Asn Lys Trp Val Ser Gln Gly Val Pro Ile Asp Gly Ile
        275                 280                 285

Gly Thr Gln Ala His Leu Ala Gly Pro Gly Gly Trp Asn Pro Ala Ser
    290                 295                 300

Gly Val Pro Ala Ala Leu Gln Ala Leu Ala Gly Ala Asn Val Lys Glu
305                 310                 315                 320

Val Ala Ile Thr Glu Leu Asp Ile Gln Gly Ala Gly Ala Asn Asp Tyr
                325                 330                 335

Val Thr Val Ala Asn Ala Cys Leu Asn Val Gln Lys Cys Val Gly Ile
            340                 345                 350

Thr Val Trp Gly Val Ser Asp Arg Asp Thr Trp Arg Ser Asn Glu Asn
        355                 360                 365

Pro Leu Leu Tyr Asp Arg Asp Tyr Arg Pro Lys Ala Ala Tyr Asn Ala
    370                 375                 380

Leu Met Asn Ala Leu
385

<210> SEQ ID NO 13
<211> LENGTH: 375
<212> TYPE: PRT
<213> ORGANISM: Myceliophthora thermophila

<400> SEQUENCE: 13

Met His Leu Ser Ser Ser Leu Leu Leu Ala Ala Leu Pro Leu Gly
1               5                   10                  15

Ile Ala Gly Lys Gly Lys Gly His Gly His Gly Pro His Thr Gly Leu
                20                  25                  30

His Thr Leu Ala Lys Gln Ala Gly Leu Lys Tyr Phe Gly Ser Ala Thr
            35                  40                  45

Asp Ser Pro Gly Gln Arg Glu Arg Ala Gly Tyr Glu Asp Lys Tyr Ala
50                  55                  60

Gln Tyr Asp Gln Ile Met Trp Lys Ser Gly Glu Phe Gly Leu Thr Thr
65                  70                  75                  80

Pro Thr Asn Gly Gln Lys Trp Leu Phe Thr Glu Pro Glu Arg Gly Val
                85                  90                  95

Phe Asn Phe Thr Glu Gly Asp Ile Val Thr Asn Leu Ala Arg Lys His
            100                 105                 110

Gly Phe Met Gln Arg Cys His Ala Leu Val Trp His Ser Gln Leu Ala
        115                 120                 125

Pro Trp Val Glu Ser Thr Glu Trp Thr Pro Glu Glu Leu Arg Gln Val
    130                 135                 140

Ile Val Asn His Ile Thr His Val Ala Gly Tyr Tyr Lys Gly Lys Cys
145                 150                 155                 160

Tyr Ala Trp Asp Val Val Asn Glu Ala Leu Asn Glu Asp Gly Thr Tyr
                165                 170                 175
```

```
Arg Glu Ser Val Phe Tyr Lys Val Leu Gly Glu Asp Tyr Ile Lys Leu
            180                 185                 190

Ala Phe Glu Thr Ala Ala Lys Val Asp Pro His Ala Lys Leu Tyr Tyr
            195                 200                 205

Asn Asp Tyr Asn Leu Glu Ser Pro Ser Ala Lys Thr Glu Gly Ala Lys
210                 215                 220

Arg Ile Val Lys Met Leu Lys Asp Ala Gly Ile Arg Ile Asp Gly Val
225                 230                 235                 240

Gly Leu Gln Ala His Leu Val Ala Glu Ser His Pro Thr Leu Asp Glu
            245                 250                 255

His Ile Asp Ala Ile Lys Gly Phe Thr Glu Leu Gly Val Glu Val Ala
            260                 265                 270

Leu Thr Glu Leu Asp Ile Arg Leu Ser Ile Pro Ala Asn Ala Thr Asn
            275                 280                 285

Leu Ala Gln Gln Arg Glu Ala Tyr Lys Asn Val Val Gly Ala Cys Val
            290                 295                 300

Gln Val Arg Gly Cys Ile Gly Val Glu Ile Trp Asp Phe Tyr Asp Pro
305                 310                 315                 320

Phe Ser Trp Val Pro Ala Thr Phe Pro Gly Gln Gly Ala Pro Leu Leu
            325                 330                 335

Trp Phe Glu Asp Phe Ser Lys His Pro Ala Tyr Asp Gly Val Val Glu
            340                 345                 350

Ala Leu Thr Asn Arg Thr Thr Gly Gly Cys Lys Gly Lys Gly Lys Gly
            355                 360                 365

Lys Gly Lys Val Trp Lys Ala
            370                 375

<210> SEQ ID NO 14
<211> LENGTH: 226
<212> TYPE: PRT
<213> ORGANISM: Myceliophthora thermophila

<400> SEQUENCE: 14

Met Val Thr Leu Thr Arg Leu Ala Val Ala Ala Ala Met Ile Ser
1               5                   10                  15

Ser Thr Gly Leu Ala Ala Pro Thr Pro Glu Ala Gly Pro Asp Leu Pro
            20                  25                  30

Asp Phe Glu Leu Gly Val Asn Asn Leu Ala Arg Arg Ala Leu Asp Tyr
        35                  40                  45

Asn Gln Asn Tyr Arg Thr Ser Gly Asn Val Asn Tyr Ser Pro Thr Asp
    50                  55                  60

Asn Gly Tyr Ser Val Ser Phe Ser Asn Ala Gly Asp Phe Val Val Gly
65                  70                  75                  80

Lys Gly Trp Arg Thr Gly Ala Thr Arg Asn Ile Thr Phe Ser Gly Ser
            85                  90                  95

Thr Gln His Thr Ser Gly Thr Val Leu Val Ser Val Tyr Gly Trp Thr
            100                 105                 110

Arg Asn Pro Leu Ile Glu Tyr Tyr Val Gln Glu Tyr Thr Ser Asn Gly
        115                 120                 125

Ala Gly Ser Ala Gln Gly Glu Lys Leu Gly Thr Val Glu Ser Asp Gly
    130                 135                 140

Gly Thr Tyr Glu Ile Trp Arg His Gln Gln Val Asn Gln Pro Ser Ile
145                 150                 155                 160

Glu Gly Thr Ser Thr Phe Trp Gln Tyr Ile Ser Asn Arg Val Ser Gly
```

165                 170                 175
Gln Arg Pro Asn Gly Gly Thr Val Thr Leu Ala Asn His Phe Ala Ala
                180                 185                 190

Trp Gln Lys Leu Gly Leu Asn Leu Gly Gln His Asp Tyr Gln Val Leu
            195                 200                 205

Ala Thr Glu Gly Trp Gly Asn Ala Gly Gly Ser Ser Gln Tyr Thr Val
        210                 215                 220

Ser Gly
225

<210> SEQ ID NO 15
<211> LENGTH: 225
<212> TYPE: PRT
<213> ORGANISM: Thermomyces lanuginosus

<400> SEQUENCE: 15

Met Val Gly Phe Thr Pro Val Ala Leu Ala Ala Leu Ala Ala Thr Gly
1               5                   10                  15

Ala Leu Ala Phe Pro Ala Gly Asn Ala Thr Glu Leu Glu Lys Arg Gln
                20                  25                  30

Thr Thr Pro Asn Ser Glu Gly Trp His Asp Gly Tyr Tyr Tyr Ser Trp
            35                  40                  45

Trp Ser Asp Gly Gly Ala Gln Ala Thr Tyr Thr Asn Leu Glu Gly Gly
        50                  55                  60

Thr Tyr Glu Ile Ser Trp Gly Asp Gly Gly Asn Leu Val Gly Gly Lys
65                  70                  75                  80

Gly Trp Asn Pro Gly Leu Asn Ala Arg Ala Ile His Phe Glu Gly Val
                85                  90                  95

Tyr Gln Pro Asn Gly Asn Ser Tyr Leu Ala Val Tyr Gly Trp Thr Arg
            100                 105                 110

Asn Pro Leu Val Glu Tyr Tyr Ile Val Glu Asn Phe Gly Thr Tyr Asp
        115                 120                 125

Pro Ser Ser Gly Ala Thr Asp Leu Gly Thr Val Glu Cys Asp Gly Ser
    130                 135                 140

Ile Tyr Arg Leu Gly Lys Thr Thr Arg Val Asn Ala Pro Ser Ile Asp
145                 150                 155                 160

Gly Thr Gln Thr Phe Asp Gln Tyr Trp Ser Val Arg Gln Asp Lys Arg
                165                 170                 175

Thr Ser Gly Thr Val Gln Thr Gly Cys His Phe Asp Ala Trp Ala Arg
            180                 185                 190

Ala Gly Leu Asn Val Asn Gly Asp His Tyr Tyr Gln Ile Val Ala Thr
        195                 200                 205

Glu Gly Tyr Phe Ser Ser Gly Tyr Ala Arg Ile Thr Val Ala Asp Val
    210                 215                 220

Gly
225

<210> SEQ ID NO 16
<211> LENGTH: 237
<212> TYPE: PRT
<213> ORGANISM: Aspergillus aculeatus

<400> SEQUENCE: 16

Met Lys Ala Phe Tyr Phe Leu Ala Ser Leu Ala Gly Ala Ala Val Ala
1               5                   10                  15

Gln Gln Thr Gln Leu Cys Asp Gln Tyr Ala Thr Tyr Thr Gly Ser Val

-continued

```
                20                  25                  30
Tyr Thr Ile Asn Asn Leu Trp Gly Lys Asp Ala Gly Ser Gly Ser
             35                  40                  45

Gln Cys Thr Thr Val Asn Ser Ala Ser Ser Ala Gly Thr Ser Trp Ser
 50                  55                  60

Thr Lys Trp Asn Trp Ser Gly Gly Glu Asn Ser Val Lys Ser Tyr Ala
 65                  70                  75                  80

Asn Ser Gly Leu Ser Phe Asn Lys Lys Leu Val Ser Gln Ile Ser Arg
                 85                  90                  95

Ile Pro Thr Ala Ala Gln Trp Ser Tyr Asp Asn Thr Gly Ile Arg Ala
                100                 105                 110

Asp Val Ala Tyr Asp Leu Phe Thr Ala Ala Asp Ile Asn His Val Thr
            115                 120                 125

Trp Ser Gly Asp Tyr Glu Leu Met Ile Trp Leu Ala Arg Tyr Gly Gly
            130                 135                 140

Val Gln Pro Leu Gly Ser Lys Ile Ala Thr Ala Thr Val Glu Gly Gln
145                 150                 155                 160

Thr Trp Glu Leu Trp Tyr Gly Val Asn Gly Ala Gln Lys Thr Tyr Ser
                165                 170                 175

Phe Val Ala Pro Thr Pro Ile Thr Ser Phe Gln Gly Asp Val Asn Asp
            180                 185                 190

Phe Phe Lys Tyr Leu Thr Gln Asn His Gly Phe Pro Ala Ser Ser Gln
            195                 200                 205

Tyr Leu Ile Thr Leu Gln Phe Gly Thr Glu Pro Phe Thr Gly Gly Pro
        210                 215                 220

Ala Thr Leu Thr Val Ser Asp Trp Ser Ala Ser Val Gln
225                 230                 235

<210> SEQ ID NO 17
<211> LENGTH: 347
<212> TYPE: PRT
<213> ORGANISM: T. reesei
<220> FEATURE:
<221> NAME/KEY: PEPTIDE
<222> LOCATION: (1)..(347)

<400> SEQUENCE: 17

Met Lys Ala Asn Val Ile Leu Cys Leu Leu Ala Pro Leu Val Ala Ala
 1               5                  10                  15

Leu Pro Thr Glu Thr Ile His Leu Asp Pro Glu Leu Ala Ala Leu Arg
                20                  25                  30

Ala Asn Leu Thr Glu Arg Thr Ala Asp Leu Trp Asp Arg Gln Ala Ser
             35                  40                  45

Gln Ser Ile Asp Gln Leu Ile Lys Arg Lys Gly Lys Leu Tyr Phe Gly
 50                  55                  60

Thr Ala Thr Asp Arg Gly Leu Leu Gln Arg Glu Lys Asn Ala Ala Ile
 65                  70                  75                  80

Ile Gln Ala Asp Leu Gly Gln Val Thr Pro Glu Asn Ser Met Lys Trp
                 85                  90                  95

Gln Ser Leu Glu Asn Asn Gln Gly Gln Leu Asn Trp Gly Asp Ala Asp
                100                 105                 110

Tyr Leu Val Asn Phe Ala Gln Gln Asn Gly Lys Ser Ile Arg Gly His
            115                 120                 125

Thr Leu Ile Trp His Ser Gln Leu Pro Ala Trp Val Asn Asn Ile Asn
        130                 135                 140
```

-continued

```
Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 18
<211> LENGTH: 419
<212> TYPE: PRT
<213> ORGANISM: T.reesei
<220> FEATURE:
<221> NAME/KEY: PEPTIDE
<222> LOCATION: (1)..(419)

<400> SEQUENCE: 18

Met Asn Lys Pro Met Ser Ser Leu Leu Leu Ala Ala Thr Leu Leu Ala
1               5                   10                  15

Gly Gly Ser Ile Ala Gln Gln Thr Val Trp Gly Gln Cys Gly Gly Gln
            20                  25                  30

Gly Trp Ser Gly Pro Thr Ser Cys Val Ala Gly Ser Ala Cys Ser Thr
        35                  40                  45

Leu Asn Pro Tyr Tyr Ala Gln Cys Ile Pro Gly Ala Thr Thr Met Ser
    50                  55                  60

Thr Thr Thr Lys Pro Thr Ser Val Ser Ala Thr Thr Arg Ala Ser
65                  70                  75                  80

Ala Thr Ser Ser Ala Thr Pro Pro Ser Ser Gly Leu Thr Arg Phe
                85                  90                  95

Ala Gly Val Asn Ile Ala Gly Phe Asp Phe Gly Cys Gly Thr Asp Gly
            100                 105                 110

Thr Cys Val Thr Ser Lys Val Tyr Pro Pro Leu Lys Asn Tyr Ala Gly
        115                 120                 125

Thr Asn Asn Tyr Pro Asp Gly Val Gly Gln Met Gln His Phe Val Asn
    130                 135                 140

Asp Asp Lys Leu Thr Ile Phe Arg Leu Pro Val Gly Trp Gln Tyr Leu
145                 150                 155                 160
```

Val Asn Asn Asn Leu Gly Gly Thr Leu Asp Ser Asn Phe Gly Lys
            165                 170                 175

Tyr Asp Gln Leu Val Gln Ala Cys Leu Ser Leu Gly Val Tyr Cys Ile
            180                 185                 190

Val Asp Ile His Asn Tyr Ala Arg Trp Asn Gly Gly Ile Ile Gly Gln
            195                 200                 205

Gly Gly Pro Thr Asn Asp Gln Phe Thr Ser Leu Trp Ser Gln Leu Ala
        210                 215                 220

Gln Lys Tyr Ala Ser Gln Ser Lys Val Trp Phe Gly Ile Met Asn Glu
225                 230                 235                 240

Pro His Asp Val Asn Ile Asn Thr Trp Ala Thr Thr Val Gln Ala Val
            245                 250                 255

Val Thr Ala Ile Arg Asn Ala Gly Ala Thr Ser Gln Phe Ile Ser Leu
            260                 265                 270

Pro Gly Asn Asp Trp Gln Ser Ala Gly Ala Phe Ile Ser Asp Gly Ser
        275                 280                 285

Ala Ala Ala Leu Ser Gln Val Lys Asn Pro Asp Gly Ser Thr Pro Asn
290                 295                 300

Leu Ile Phe Asp Leu His Lys Tyr Leu Asp Ser Asp Asn Ser Gly Thr
305                 310                 315                 320

His Ala Asp Cys Val Thr Asn Asn Val Asn Asp Ala Phe Ser Pro Val
            325                 330                 335

Ala Thr Trp Leu Arg Gln Asn Asn Arg Gln Ala Ile Leu Thr Glu Thr
            340                 345                 350

Gly Gly Gly Asn Thr Gln Ser Cys Ile Gln Tyr Leu Cys Gln Gln Phe
        355                 360                 365

Gln Tyr Ile Asn Gln Asn Ser Asp Val Tyr Leu Gly Tyr Val Gly Trp
        370                 375                 380

Gly Ala Gly Ser Phe Asp Ser Thr Tyr Ile Leu Thr Glu Thr Pro Thr
385                 390                 395                 400

Gly Ser Gly Ser Ser Trp Thr Asp Thr Ser Leu Val Ser Ser Cys Ile
            405                 410                 415

Ser Arg Lys

<210> SEQ ID NO 19
<211> LENGTH: 459
<212> TYPE: PRT
<213> ORGANISM: T.viride
<220> FEATURE:
<221> NAME/KEY: PEPTIDE
<222> LOCATION: (1)..(459)

<400> SEQUENCE: 19

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
            20                  25                  30

His Pro Lys Leu Thr Thr Tyr Lys Cys Thr Lys Ser Gly Gly Cys Val
        35                  40                  45

Ala Gln Asp Thr Ser Val Val Leu Asp Trp Asn Tyr Arg Trp Met His
50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
            85                  90                  95

-continued

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
            115                 120                 125

Pro Arg Leu Tyr Leu Leu Asp Ser Asp Gly Glu Tyr Val Met Leu Lys
130                 135                 140

Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
            180                 185                 190

Cys Asp Ala Gln Cys Pro Val Gln Thr Trp Arg Asn Gly Thr Leu Asn
            195                 200                 205

Thr Ser His Gln Gly Phe Cys Cys Asn Glu Met Asp Ile Leu Glu Gly
            210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
            260                 265                 270

Ile Ile Thr Gln Phe Asn Thr Asp Asn Gly Ser Pro Ser Gly Asn Leu
            275                 280                 285

Val Gly Ile Thr Arg Lys Tyr Gln Gln Asn Gly Val Asp Ile Pro Ser
            290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
            340                 345                 350

Asp Ser Gly Asn Ala Gly Pro Cys Ser Ser Thr Glu Gly Asn Pro Ser
            355                 360                 365

Asn Ile Leu Ala Asn Asn Pro Asn Thr His Val Val Phe Ser Asn Ile
            370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
            420                 425                 430

Gly Ile Gly Tyr Ser Gly Cys Lys Thr Cys Thr Ser Gly Thr Thr Cys
            435                 440                 445

Gln Tyr Ser Asn Asp Tyr Tyr Ser Gln Cys Leu
            450                 455

<210> SEQ ID NO 20
<211> LENGTH: 232
<212> TYPE: PRT
<213> ORGANISM: T.reesei
<220> FEATURE:
<221> NAME/KEY: PEPTIDE
<222> LOCATION: (1)..(232)

```
<400> SEQUENCE: 20

Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala His Ala Asp Trp Gln Trp
    50                  55                  60

Ser Gly Gly Gln Asn Asn Val Lys Ser Tyr Gln Asn Ser Gln Ile Ala
65                  70                  75                  80

Ile Pro Gln Lys Arg Thr Val Asn Ser Ile Ser Ser Met Pro Thr Thr
                85                  90                  95

Ala Ser Trp Ser Tyr Ser Gly Ser Asn Ile Arg Ala Asn Val Ala Tyr
            100                 105                 110

Asp Leu Phe Thr Ala Ala Asn Pro Asn His Val Thr Tyr Ser Gly Asp
            115                 120                 125

Tyr Glu Leu Met Ile Trp Leu Gly Lys Tyr Gly Asp Ile Gly Pro Ile
        130                 135                 140

Gly Ser Ser Gln Gly Thr Val Asn Val Gly Gly Gln Ser Trp Thr Leu
145                 150                 155                 160

Tyr Tyr Gly Tyr Asn Gly Ala Met Gln Val Tyr Ser Phe Val Ala Gln
                165                 170                 175

Thr Asn Thr Thr Asn Tyr Ser Gly Asp Val Lys Asn Phe Phe Asn Tyr
            180                 185                 190

Leu Arg Asp Asn Lys Gly Tyr Asn Ala Ala Gly Gln Tyr Val Leu Ser
        195                 200                 205

Tyr Gln Phe Gly Thr Glu Pro Phe Thr Gly Ser Gly Thr Leu Asn Val
        210                 215                 220

Ala Ser Trp Thr Ala Ser Ile Asn
225                 230
```